US012694276B2

(12) United States Patent
Kurihara et al.

(10) Patent No.: US 12,694,276 B2
(45) Date of Patent: Jul. 28, 2026

(54) DIAGNOSIS SUPPORT DEVICE, LEARNING DEVICE, DIAGNOSIS SUPPORT METHOD, LEARNING METHOD, AND PROGRAM

(71) Applicant: NIKON CORPORATION, Tokyo (JP)

(72) Inventors: Toshihide Kurihara, Tokyo (JP); Yusaku Katada, Tokyo (JP); Kazuo Tsubota, Tokyo (JP); Kanato Masayoshi, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 18/424,102

(22) Filed: Jan. 26, 2024

(65) Prior Publication Data

US 2024/0249122 A1 Jul. 25, 2024

Related U.S. Application Data

(63) Continuation of application No. 16/930,510, filed on Jul. 16, 2020, now abandoned, which is a (Continued)

(30) Foreign Application Priority Data

Jan. 19, 2018 (JP) ................................. 2018-007585

(51) Int. Cl.
*G06N 3/00* (2023.01)
*A61B 3/00* (2006.01)
(Continued)

(52) U.S. Cl.
CPC ........... *G06N 3/047* (2023.01); *A61B 3/0025* (2013.01); *A61B 3/1241* (2013.01); *A61B 5/1128* (2013.01)

(58) Field of Classification Search
CPC .... G06N 3/047; A61B 3/0025; A61B 3/1241; A61B 3/1128
See application file for complete search history.

(56) References Cited

U.S. PATENT DOCUMENTS 7,290,880 B1    11/2007  Yaron et al.
9,275,283 B2     3/2016  Shibutani
(Continued)

FOREIGN PATENT DOCUMENTS

EP          3300654 A2 *  4/2018  ........... G06T 1/0007
EP          3 741 288 A1   11/2020
(Continued)

OTHER PUBLICATIONS

EPO Examination Report for Application No. 24212000.4 dated Nov. 10, 2025 (6 pages).
(Continued)

*Primary Examiner* — Khai M Nguyen
(74) *Attorney, Agent, or Firm* — Foley & Lardner LLP

(57) ABSTRACT

A device for supporting diagnosis has: a reception unit that is configured to receive a fundus image of a subject eye; an identification unit provided with a trained model that is configured to recognize, in the fundus image of the subject eye, an area of abnormality in blood circulation, wherein the model has been trained based upon an image of a fundus and an area of abnormality in blood circulation specified in a fluorescent angiography image of the fundus; and an output unit that is configured to output information relating to the area of abnormality in blood circulation recognized in the fundus image of the subject eye.

13 Claims, 14 Drawing Sheets

Related U.S. Application Data continuation of application No. PCT/JP2019/001470, filed on Jan. 18, 2019.

(51) Int. Cl.

| | | |
|---|---|---|
| *A61B 3/12* | (2006.01) | |
| *A61B 5/11* | (2006.01) | |
| *G06N 3/047* | (2023.01) | |

(56) References Cited

U.S. PATENT DOCUMENTS

| | | | |
|---|---|---|---|
| 2013/0165771 A1* | 6/2013 | Ni | A61K 49/0043 |
| | | | 600/431 |
| 2014/0314288 A1 | 10/2014 | Roychowdhury et al. | |
| 2016/0071266 A1 | 3/2016 | Srivastava et al. | |
| 2016/0278627 A1 | 9/2016 | Huang et al. | |
| 2018/0303337 A1* | 10/2018 | Li | A61B 3/14 |
| 2019/0191988 A1* | 6/2019 | Gargeya | A61B 3/1241 |
| 2020/0246181 A1* | 8/2020 | Xiao | G02C 7/041 |
| 2021/0000343 A1 | 1/2021 | Kurihara et al. | |
| 2023/0316522 A1* | 10/2023 | Boyd | A61B 3/12 |
| | | | 382/130 |

FOREIGN PATENT DOCUMENTS

| | | | |
|---|---|---|---|
| JP | 2008079682 A * | 4/2008 | |
| JP | 6090505 B1 | 3/2017 | |
| JP | 2010-178802 A | 8/2020 | |
| JP | 7704263 B2 | 7/2025 | |
| WO | WO-2017/031099 A1 | 2/2017 | |

OTHER PUBLICATIONS

European Search Report for EP Appl. Ser. No. 24212000.4 dated Feb. 3, 2025 (6 pages).

Extended European Search Report issued in corresponding European Application No. 19741888.2 dated Oct. 25, 2021 (12 pages).

International Search Report issued in corresponding application No. PCT/JP2019/001470 dated Mar. 19, 2019 with English translation.

Ghasemi Kamasi Zeinab et al., "Non-Rigid Registration of Fluorescein Angiography and Optical Coherence Tomography via Scanning Laser Ophthalmoscope Imaging", 2017 39th Annual International Conference of the IEEE Engineering in Medicine and Biology Society (EMBC), IEEE, Jul. 11, 2017, pp. 4415-4418.

Office Action issued in corresponding Chinese Patent Application No. 201980018367.7 dated May 25, 2023 (24 pages).

Office Action issued in corresponding Japanese Patent Application No. 2022-147056 dated Nov. 14, 2023 (5 pages).

Abhijit Guha Roy et al., "ReLayNet: Retinal Layer and Fluid Segmentation of Macular Optical Coherence Tomography using Fully Convolutional Network", arxiv.org, Cornell University Library, 201 Olin Library Cornell University Ithaca, NY 14853, Apr. 7, 2017, pp. 1-24.

Written Opinion of the International Search Authority issued in corresponding application No. PCT/JP2019/001470 dated Mar. 19, 2019 with English translation.

Office Action issued in corresponding Japanese Patent Application No. 2025-107448 dated May 19, 2026 (4 pages).

Office Action issued in corresponding European Patent Application No. 24212000.4 dated Jun. 18, 2026 (6 pages).

* cited by examiner

FIG. 3

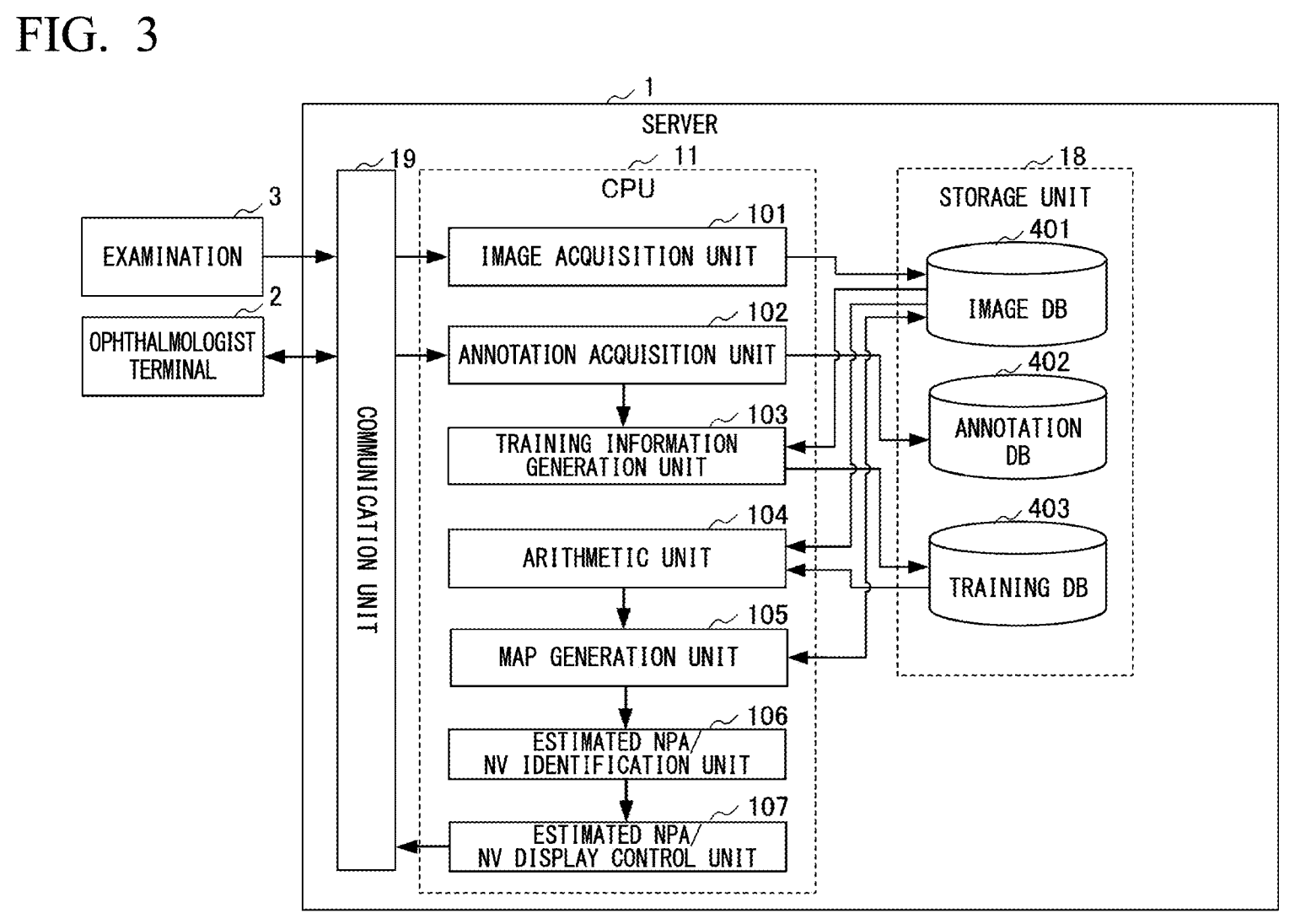

SERVER 1

11 CPU

101 IMAGE ACQUISITION UNIT

102 ANNOTATION ACQUISITION UNIT

103 TRAINING INFORMATION GENERATION UNIT

104 ARITHMETIC UNIT

105 MAP GENERATION UNIT

106 ESTIMATED NPA/NV IDENTIFICATION UNIT

107 ESTIMATED NPA/NV DISPLAY CONTROL UNIT

18 STORAGE UNIT

401 IMAGE DB

402 ANNOTATION DB

403 TRAINING DB

19 COMMUNICATION UNIT

3 EXAMINATION

2 OPHTHALMOLOGIST TERMINAL

DIAGNOSIS SUPPORT DEVICE, LEARNING DEVICE, DIAGNOSIS SUPPORT METHOD, LEARNING METHOD, AND PROGRAM

The present invention relates to a diagnosis support device, a learning device, a diagnosis support method, a learning method, and a program.

This application is a continuation of U.S. Application Ser. No. 16/930,510, filed Jul. 16, 2020, which is a continuation of International Application No. PCT/JP2019/001470, filed Jan. 18, 2019, which claims priority to Japanese Patent Application No. 2018-007585, filed Jan. 19, 2018, the entire contents of each are incorporated herein by reference.

TECHNICAL FIELD

Background Art

Diabetic retinopathy is an important disease that is the second leading cause of blindness in Japan, but subjective symptoms do not appear until the stage of the disease has progressed considerably, and thus, early detection and early treatment at medical examinations, or the like, is important. To solve this problem, a fundus image analysis system that emphasizes a capillary blood vessel aneurysm that shows an initial change in diabetic retinopathy (see Patent Document 1) and an image analysis system that screens diabetic retinopathy from fundus images (see Patent Document 2) have been proposed.

CITATION LIST

Patent Literature

Patent Document 1

Japanese Unexamined Patent Application, First Publication No. 2010-178802

Patent Document 2

United States Patent Application, Publication No. 2014/0314288

SUMMARY OF INVENTION

Technical Problem

The techniques proposed in Patent Document 1 and Patent Document 2 are aimed at discovery and screening of diseases as described above. On the other hand, advancing one step from the disease screening of the diabetic retinopathy, in the case of the stage of medical treatment or cure of diabetic retinopathy patients, it has become clear that the diabetic retinopathy is caused by an ischemic state due to vascular disorder associated with hyperglycemia so that the diabetic retinopathy is progressing, and thus, it is most important to understand retinal circulatory dynamics. In order to understand the retinal circulatory dynamics, angiography of retina such as fundus fluorescein angiography is essential. However, due to its risk, invasiveness, and geographical restrictions limited to large hospitals, the angiography of retina is a burdensome examination for both patients and medical staffs, which causes hesitancy to take pictures of patients with good eyesight and patients with reduced physical functions, to perform repeated imaging, or the like. For this reason, there is a problem that in many cases, detection of symptom appearances and disease states is delayed, and the treatment is delayed. The same problem appears in all ocular ischemic diseases represented by diabetic retinopathy. OCT angiography is a non-invasive device for understanding retinal circulation abnormality, but unlike the contrast examination, the OCT angiography cannot detect the blood flow dynamics and cannot detect the whole image of the retina due to a narrow angle of view while being effective for local diseases such as a macular disease. Accordingly, it is not suitable for detecting the retinal circulatory dynamics of ocular ischemic diseases such as diabetic retinopathy.

The present invention has been made in view of such circumstances, and an object of the present invention is to quickly and easily recognize abnormal circulatory findings from a fundus image without performing fundus fluorescein angiography.

Solution to Problem (1) According to an aspect of the present invention, there is provided a diagnosis support device including: a identification unit that is configured to recognize an area of abnormality in blood circulation in a fundus image that is an image of a fundus, using a trained model obtained by learning a relationship between the fundus image and the area of abnormality in blood circulation in the fundus image, on the basis of the fundus image and the area of abnormality in blood circulation specified on the basis of a fluorescein angiography image of the fundus; and an output unit output information indicating the fundus image of a patient and the area of abnormality in blood circulation in the fundus image of the patient identified by the identification unit using the trained model.

(2) According to the aspect of the present invention, in the diagnosis support device according to (1), the area of abnormality in blood circulation is generated on the basis of the fluorescein angiography image and an ophthalmologist's diagnostic note regarding one or both of a retinal non-perfusion area and a neovascularization attached to the fluorescein angiography image.

(3) According to the aspect of the present invention, in the diagnosis support device according to (1) or (2), the identification unit is configured to recognize one or both of a retinal non-perfusion area and an area corresponding to a neovascularization in the fundus image.

(4) According to the aspect of the present invention, in the diagnosis support device according to any one of (1) to (3), the output unit is configured to output an image in which the area of abnormality in blood circulation identified by the identification unit is overlaid on the fundus image.

(5) According to another aspect of the present invention, a learning device includes: a learning unit that generates, on the basis of a fundus image that is an image of a fundus and an area of abnormality in blood circulation specified on the basis of a fluorescein angiography image of the fundus, a trained model indicating a relationship between the fundus image and the area of abnormality in blood circulation in the fundus image, through learning.

(6) According to the aspect of the present invention, in the learning device according to (5), the area of abnormality in blood circulation is generated on the basis of the fluorescein angiography image, and an ophthalmologist's diagnostic note regarding one or both of the retinal non-perfusion area and the neovascularization attached to the fluorescein angiography image.

(7) According to still another aspect of the present invention, there is provided a diagnosis support method executed by a diagnosis support device, the method including: recognizing an area of abnormality in blood circulation in a fundus image that is an image of a fundus, using a trained model obtained by learning a relationship between the fundus image and the area of abnormality in blood circulation in the fundus image, on the basis of the fundus image and the area of abnormality in blood circulation specified on the basis of a fluorescein angiography image of the fundus; and outputting information indicating the fundus image of a patient and the area of abnormality in blood circulation in the fundus image of the patient identified by the identification unit using the trained model.

(8) According to still another aspect of the present invention, there is provided a learning method executed by a learning device, the method including: acquiring information indicating a fundus image that is an image of a fundus, and information indicating an area of abnormality in blood circulation specified on the basis of a fluorescein angiography image of the fundus; and generating, on the basis of the acquired fundus image and the acquired area of abnormality in blood circulation specified on the basis of the fluorescein angiography image of the fundus, a trained model indicating a relationship between the fundus image and the area of abnormality in blood circulation in the fundus image, through learning.

(9) According to still another aspect of the present invention, there is provided a program causing a computer of a diagnosis support device to execute: recognizing an area of abnormality in blood circulation in a fundus image that is an image of a fundus, using a trained model obtained by learning a relationship between the fundus image and the area of abnormality in blood circulation in the fundus image, on the basis of the fundus image and the area of abnormality in blood circulation specified on the basis of a fluorescein angiography image of the fundus; and outputting information indicating the fundus image of a patient and the area of abnormality in blood circulation in the fundus image of the patient identified using the trained model.

(10) According to still another aspect of the present invention, there is provided a program causing a computer of a learning device to execute: acquiring information indicating a fundus image that is an image of a fundus, and information indicating an area of abnormality in blood circulation specified on the basis of a fluorescein angiography image of the fundus; and generating, on the basis of the acquired fundus image and the acquired area of abnormality in blood circulation specified on the basis of the fluorescein angiography image of the fundus, a trained model indicating a relationship between the fundus image and the area of abnormality in blood circulation in the fundus image, through learning.

In the present invention, the "fundus image" means an image obtained by imaging the fundus of a patient with a fundus camera in order to make a diagnosis regarding a disease of an ophthalmological system, and the "fluorescein angiography image" means an image obtained by continuously taking a photograph of the fundus using an excitation light and a filter corresponding to fluorescence dye while injecting the fluorescence dye through a vein of the patient's arm and taking a contrast image of a circulating state of the fundus.

Advantageous Effects of Invention

According to the present invention, it is possible to predict abnormal circulatory findings from a fundus image easily, without performing fundus fluorescein angiography.

BRIEF DESCRIPTION OF DRAWINGS

FIG. 3 is a diagram illustrating an example of a functional configuration for realizing various processes such as an NPA/NV existence probability map generating process, an accompanying finding existence probability map generating process, an estimated NPA/NV recognizing process, and an estimated NPA/NV display process in a functional configuration of the server shown in FIG. 2.

FIG. 5 is a diagram illustrating a flow of various kinds of information used in the processes executed by the server shown in FIG. 3.

FIG. 15 is a diagram illustrating an example of a structure of a neural network.

DESCRIPTION OF EMBODIMENTS

Embodiments of the present invention will be described below with reference to the accompanying drawings.

Figure 1:
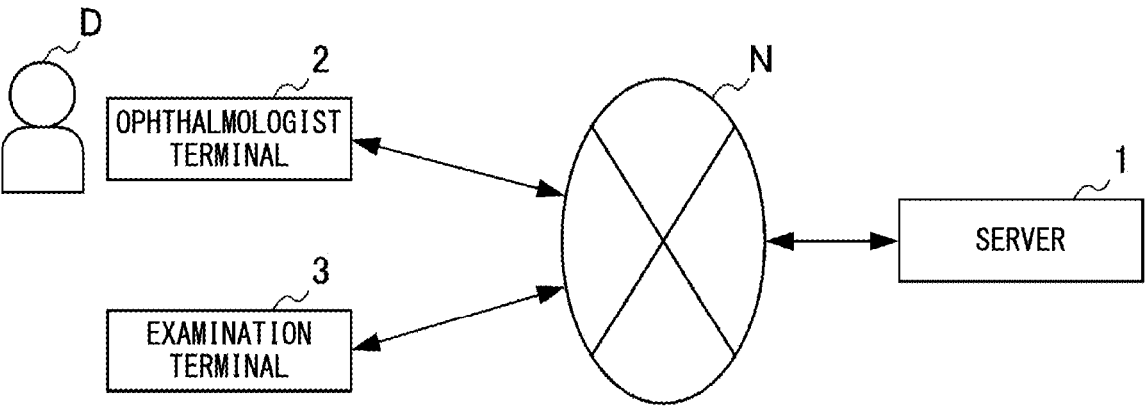
FIG. 1 is a configuration diagram illustrating an information processing system including a server that is an embodiment of an information processing device of the present invention.

FIG. 1 is a configuration diagram illustrating an information processing system including a server 1 that is an embodiment of an information processing device of the present invention.

The information processing system shown in FIG. 1 is configured to include the server 1, an ophthalmologist terminal 2, and an examination device 3.

The server 1, the ophthalmologist terminal 2, and the examination device 3 are connected to each other through a network N such as the Internet.

The server 1 is a server that manages the information processing system shown in FIG. 1, and executes various processes such as an NPA/NV existence probability map generating process, an accompanying finding existence probability map generating process, and an estimated NPA/NV recognizing process. The content of specific processes executed by the server 1 will be described later with reference to FIG. 3.

The "NPA/NV existence probability map generating process" is a series of processes executed by the server 1 from generation of NPA/NV training information to generation of an NPA/NV existence probability map.

The "NPA/NV training information" refers to training information for calculating a retinal non-perfusion area (NPA/non-perfusion area) (hereinafter, referred to as "a retinal non-perfusion area" or "NPA") existence probability (hereinafter, referred to as an "NPA existence probability") and a neovascularization (NV/neovascularization) existence probability (hereinafter, referred to as an "NV existence probability"), in fundus image information of a patient. Specifically, the "NPA/NV training information" is generated on the basis of fluorescein angiography image information and NPA/NV annotation information attached to the fluorescein angiography image information.

The "retinal non-perfusion area" refers to a poor circulatory area of the retina that results from retinal vessel occlusion in ocular ischemic diseases.

The "NPA/NV existence probability map" is image information in which the NPA existence probability and the NV existence probability are identifiably displayed in fundus image information.

The "fundus image information" refers to image information based on a fundus image.

The "fluorescein angiography image information" refers to information based on a fluorescein angiography image.

The "NPA/NV annotation information" refers to a diagnostic note of an ophthalmologist D, attached to fluorescein angiography image information, regarding at least one of a retinal non-perfusion area (NPA) or a neovascularization (NV).

The "neovascularization" means that poor retinal circulation and ischemia have further progressed in the retinal non-perfusion area. In a case where bleeding or retinal detachment through proliferative membrane formation occurs from the neovascularization, it eventually leads to blindness, and thus, it is very important to specify a poor circulatory area of the retina such as a retinal non-perfusion area or a neovascularization.

In addition, a specific processing flow of the NPA/NV existence probability map generating process will be described later with reference to a flowchart of FIG. 4.

The "accompanying finding existence probability map generating process" refers to a series of processes executed by the server 1 from generation of the accompanying finding training information to generation of the accompanying finding existence probability map.

The "accompanying finding training information" refers to training information in calculating an accompanying finding existence probability in fundus image information of a patient. Specifically, the "accompanying finding training information" refers to training information generated on the basis of the fluorescein angiography image information and the fundus image information, and accompanying finding annotation information attached to these image information.

The "accompanying finding annotation information" means a diagnostic note other than the diagnostic note regarding a retinal non-perfusion area (NPA) or a neovascularization (NV), among diagnostic notes indicating that the ophthalmologist D incidentally makes a judgment "not normal" with respect to the fluorescein angiography image information and the fundus image information. For example, information such as a capillary aneurysm, fundus bleeding, vitiligo, soft vitiligo, venous abnormality, intra-retinal microvascular abnormality, vitreous hemorrhage, a proliferative membrane, and retinal detachment is an example of the "accompanying finding annotation information".

The "accompanying finding existence probability map" is image information (not shown) in which the existence probability of the accompanying finding is identifiably displayed in the fundus image information.

A specific processing flow of the accompanying finding existence probability map generating process will be described later with reference to the flowchart of FIG. 4.

The "estimated NPA/NV recognizing process" refers to a series of processes from a process of recognizing an area estimated to correspond to the retinal non-perfusion area (NPA) in the fundus image information as an estimated NPA, on the basis of the NPA existence probability, and a process of recognizing an area estimated to correspond to the neovascularization (NV) in the fundus image information as an estimated NV, on the basis of the NV existence probability, in the processes executed by the server 1.

Note that a specific processing flow of the estimated NPA/NV recognizing process will be described later with reference to the flowchart of FIG. 4.

The ophthalmologist terminal 2 is an information processing device operated by the ophthalmologist D, and is configured by, for example, a personal computer or the like. The ophthalmologist terminal 2 transmits NPA/NV annotation information and accompanying finding annotation information to the server 1, and acquires information on estimated NPA/NV identified by the server 1, for example. The various types of information acquired by the ophthalmologist terminal 2 is output from the ophthalmologist terminal 2, and is used for examination by the ophthalmologist D.

The examination device 3 is configured by various devices used in eye examination of a patient. The examination device 3 transmits each of fundus image information obtained by imaging in fundus examination and fluorescein angiography image information obtained by imaging in fundus fluorescein angiography to the server 1.

Figure 2:
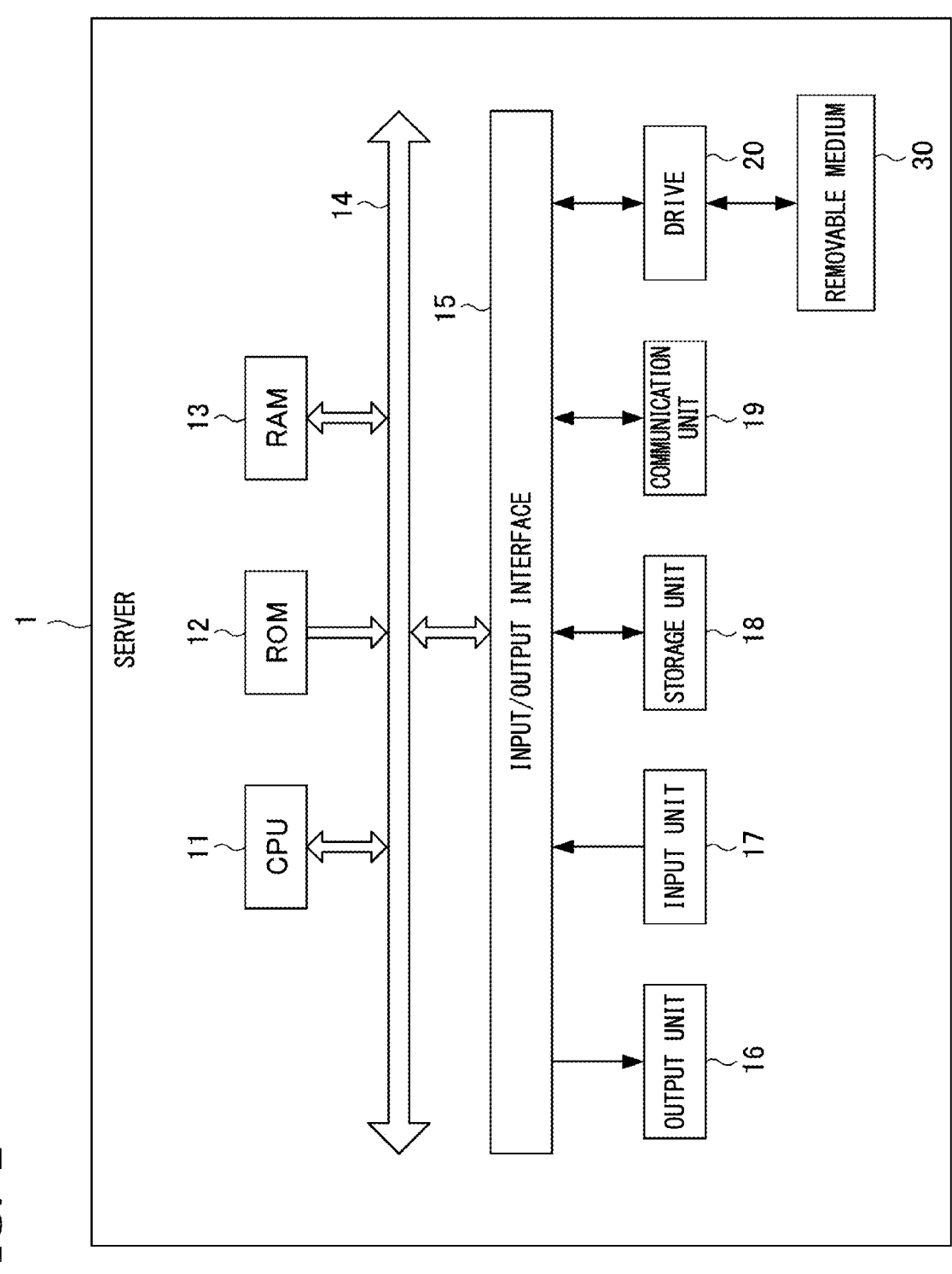
FIG. 2 is a block diagram illustrating a hardware configuration of the server in the information processing system shown in FIG. 1.

FIG. 2 is a block diagram illustrating a hardware configuration of the server 1 in the information processing system of FIG. 1.

The server 1 includes a central processing unit (CPU) 11, a read only memory (ROM) 12, a random access memory (RAM) 13, a bus 14, an input/output interface 15, an output unit 16, an input unit 17, a storage unit 18, a communication unit 19, and a drive 20.

The CPU 11 executes various processes according to a program recorded on the ROM 12 or a program loaded from the storage unit 18 into the RAM 13.

The RAM 13 also appropriately stores data and the like necessary in a case where the CPU 11 executes various processes.

The CPU 11, ROM 12, and RAM 13 are connected to each other through the bus 14. The input/output interface 15 is also connected to the bus 14. The output unit 16, the input unit 17, the storage unit 18, the communication unit 19, and the drive 20 are connected to the input/output interface 15.

The output unit 16 is configured by various liquid crystal displays or the like, and outputs various types of information.

The input unit 17 is configured by various types of hardware, through which various types of information are input.

The storage unit 18 is configured by a dynamic random access memory (DRAM) or the like, and stores various types of data.

The communication unit 19 controls communication with other devices through the network N including the Internet.

A drive 20 is provided as necessary. A removable medium 30 including a magnetic disc, an optical disc, a magneto-optical disc, a semiconductor memory, or the like is appropriately mounted on the drive 20. A program read from the removable medium 30 by the drive 20 is installed in the storage unit 18 as necessary. In addition, the removable medium 30 may also store various types of data stored in the storage unit 18, similarly to the storage unit 18.

Next, a functional configuration of the server 1 having such a hardware configuration will be described with reference to FIG. 3.

FIG. 3 is a functional block diagram illustrating an example of a functional configuration for realizing the NPA/NV existence probability map generating process, the accompanying finding existence probability map generating process, the estimated NPA/NV recognizing process, and the estimated NPA/NV display process in the functional configuration of the server 1 of FIG. 2, in the information processing system of FIG. 1.

As shown in FIG. 3, in the CPU 11 (FIG. 2) of the server 1, in a case where the NPA/NV existence probability map generating process is executed, an image acquisition unit 101, an annotation acquisition unit 102, a training information generation unit 103, and an arithmetic unit 104 perform their functions.

In a case where the accompanying finding existence probability map generating process is executed, the image acquisition unit 101, the annotation acquisition unit 102, the training information generation unit 103, and the arithmetic unit 104 perform their functions.

In a case where the estimated NPA/NV recognizing process is executed, an estimated NPA/NV identification unit 106 performs its function.

In a case where the estimated NPA/NV display process is executed, an estimated NPA/NV display control unit 107 performs its function.

An image DB 401, an annotation DB 402, and a training DB 403 are provided in one area of the storage unit 18 (FIG. 2). The storage unit 18 may be disposed in the ophthalmologist terminal 2 instead of the server 1.

The image acquisition unit 101 acquires fluorescein angiography image information of a patient and fundus image information of the patient. The fluorescein angiography image information and the fundus image information acquired by the image acquisition unit 101 are respectively stored in the image DB 401 for management. Specifically, in fundus fluorescein angiography of a patient, in a case where a fluorescein angiography image of the patient is captured by the examination device 3, fluorescein angiography image information based on the fluorescein angiography image is transmitted to the server 1. Further, in the fundus examination of the patient, in a case where a fundus image of the patient is captured by the examination device 3, fundus image information based on the fundus image is transmitted to the server 1. The image acquisition unit 101 of the server 1 acquires the fluorescein angiography image information and the fundus image information transmitted from the examination device 3 to the server 1, and stores the image information in the image DB 401.

Thus, the server 1 can accurately manage the fluorescein angiography image information and the fundus image information of the patient without omission.

The annotation acquisition unit 102 acquires a diagnostic note of the ophthalmologist D, which is attached to the fluorescein angiography image information of the patient, regarding at least one of a retinal non-perfusion area (NPA) or a neovascularization (NV) as NPA/NV annotation information. Specifically, in the fundus fluorescein angiography, when the diagnostic note of the ophthalmologist D regarding the retinal non-perfusion area (NPA) and the neovascularization (NV) is attached to the fluorescein angiography image information, the ophthalmologist terminal 2 transmits the diagnostic note to the server 1 as the NPA/NV annotation information based on the operation of the ophthalmologist D. The annotation acquisition unit 102 of the server 1 acquires the NPA/NV annotation information transmitted from the ophthalmologist terminal 2, and stores the information in the annotation DB 402. The fluorescein angiography image information and the NPA/NV annotation information attached to the image information are managed in association with each other.

As a result, the server 1 can manage, without omission, the diagnostic note of the ophthalmologist D regarding at least one of the retinal non-perfusion area (NPA) or the neovascularization (NV) attached to the fluorescein angiography image information, as the NPA/NV annotation information.

In addition, the annotation acquisition unit 102 acquires the diagnostic note of the ophthalmologist D regarding an accompanying finding attached to the fluorescein angiography image and the fundus image, as accompanying finding annotation information. Specifically, in a case where the diagnostic note of the ophthalmologist D regarding the accompanying finding is attached to the fluorescein angiography image information and the fundus image information, the ophthalmologist terminal 2 transmits the diagnostic note to the server 1 as the accompanying finding annotation information on the basis of the operation of the ophthalmologist D. The annotation acquisition unit 102 of the server 1 acquires the accompanying finding annotation information transmitted from the ophthalmologist terminal 2, and stores this information in the annotation DB 402. The fluorescein angiography image information and the fundus image information, and the accompanying finding annotation information attached to these image information are managed in association with each other.

As a result, the server 1 can manage the diagnostic note of the ophthalmologist D regarding the accompanying finding attached to the fluorescein angiography image information and the fundus image information as the accompanying finding annotation information, without omission.

The training information generation unit 103 generates NPA/NV training information that serves as training information for calculating an NPA existence probability and an NV existence probability on the basis of the fluorescein angiography image information and the NPA/NV annotation information corresponding to the fluorescein angiography image information.

That is, the image DB 401 stores fluorescein angiography image information obtained from a plurality of patients, and the annotation DB 402 stores NPA/NV annotation information. The training information generation unit 103 generates NPA/NV training information which serves as training information in calculating the NPA existence probability and the NV existence probability in the fundus image information on the basis of the information stored in these databases.

Thus, the server 1 can generate and store the training information for calculating the NPA existence probability and the NV existence probability in the fundus image information of the patients.

In addition, the training information generation unit 103 generates the accompanying finding training information on the basis of the fluorescein angiography image information and the fundus image information, and the accompanying finding annotation information corresponding to these image information.

That is, the image DB 401 stores the fundus image information and the fluorescein angiography image information obtained from a plurality of patients, and the annotation DB 402 stores the accompanying finding annotation information. The training information generation unit 103 generates the accompanying finding training information that serves as training information in calculating the existence probability of the accompanying findings in the fundus image information, on the basis of the information stored in these databases.

Thus, the server 1 can store the training information for calculating the existence probability of the accompanying findings in the fundus image information of the patients.

The arithmetic unit 104 calculates the NPA existence probability and the NV existence probability on the basis of at least the NPA/NV training information. In addition, in a case where an accompanying finding existence probability map (which will be described later) is generated, the arithmetic unit 104 calculates the NPA existence probability and the NV existence probability on the basis of the accompanying finding existence probability map and the NPA/NV training information. A specific method for calculating the NPA existence probability and the NV existence probability is not particularly limited. For example, a method for calculating the NPA existence probability and the NV existence probability by extracting a feature common in the fundus images having the NPA/NV from the NPA/NV training information and normalizing the matching degree with the feature with respect to whether or not the fundus image information of the patient has the feature may be used. The NPA existence probability and the NV existence probability may be calculated using a deep learning technique.

As a result, it is possible to set a standard for recognizing an area of the fundus image information that is estimated to correspond to the retinal non-perfusion area (NPA) and an area that is estimated to correspond to the neovascularization (NV).

Further, the arithmetic unit 104 calculates the existence probability of the accompanying finding in the fundus image information on the basis of the accompanying finding training information. A specific method of calculating the existence probability of the accompanying findings is not particularly limited. For example, a method for calculating the accompanying finding existence probability by extracting a feature common in the fundus images having the accompanying finding from the accompanying finding training information and normalizing the matching degree with the feature with respect to whether or not the fundus image information of the patient has the feature may be used. The accompanying finding existence probability may be calculated using a deep learning technique.

Accordingly, it is possible to set a standard for recognizing an area of the fundus image information that is estimated to correspond to the retinal non-perfusion area (NPA) and an area that is estimated to correspond to the neovascularization (NV).

Figure 8:
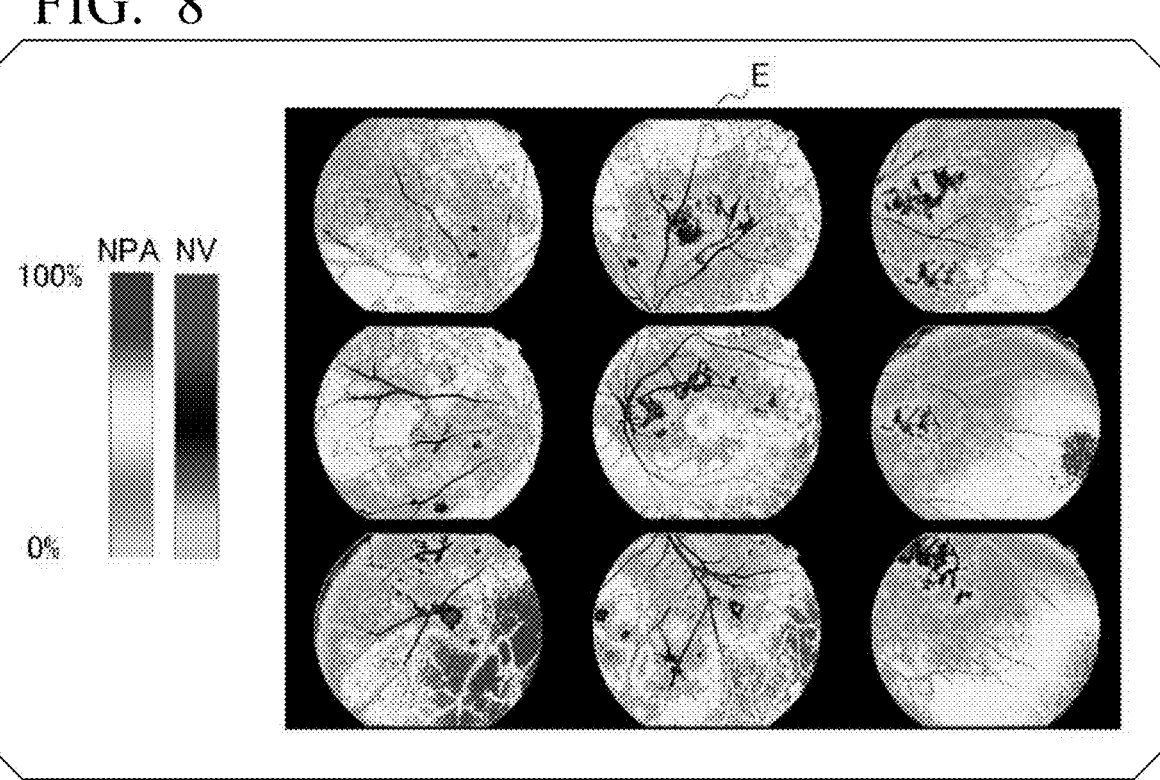
FIG. 8 is a diagram illustrating an example of an NPA/NV existence probability map output in the NPA/NV existence probability map generating process executed by the server shown in FIG. 3.

The map generation unit 105 generates an NPA/NV existence probability map as image information in which the NPA existence probability and the NV existence probability are identifiably displayed in the fundus image information. Specifically, image information such as an NPA/NV existence probability map E illustrated in FIG. 8 is generated.

Thus, it is possible to generate information that serves as a basis for estimating the existence of the retinal non-perfusion area (NPA) and the neovascularization (NV) in the fundus image information.

Note that a method of identifiably displaying the NPA existence probability and the NV existence probability in the fundus image information is not particularly limited. For example, the NPA existence probability and the NV existence probability may be identifiably displayed according to a color difference, or the NPA existence probability and the NV existence probability may be identifiably displayed according to color shades.

The map generation unit 105 also generates an accompanying finding existence probability map (not shown) as image information in which the accompanying finding existence probability is identifiably displayed the fundus image information.

Thus, it is possible to generate information that serves as a basis for estimating the existence of the retinal non-perfusion area (NPA) and the neovascularization (NV) in the fundus image information.

A method for identifiably displaying the accompanying finding existence probability in the fundus image information is not particularly limited. For example, the accompanying finding existence probability may be identifiably displayed according to a color difference, or the accompanying finding existence probability may be identifiably displayed according to color shades.

The estimated NPA/NV identification unit 106 identifies an area of the fundus image information that is estimated to correspond to the retinal non-perfusion area (NPA), as an estimated NPA, on the basis of the NPA existence probability and the NV existence probability, and identifies an area that is estimated to correspond to the neovascularization (NV), as an estimated NV. Specifically, in the fundus image information of the patient, an area in which the NPA existence probability and the NV existence probability exceed a predetermined threshold value is identified as an area that is estimated to correspond to the retinal non-perfusion area (NPA) (estimated NPA), or an area that is estimated to correspond to the neovascularization (estimated NV). Note that the threshold value may be discretionally changed according to judgment of the ophthalmologist D.

As a result, it is possible to early and easily identify an area where the existence of the retinal non-perfusion area (NPA) is estimated (estimated NPA) and an area where the existence of the neovascularization (NV) is estimated (estimated NV), in the image information based on the fundus image.

The estimated NPA/NV display control unit 107 executes a control for displaying the estimated NPA area and the estimated NV area on the fundus image information.

Thus, the area where the existence of the retinal non-perfusion is estimated (estimated NPA) and the area where the existence of the neovascularization (NV) is estimated (estimated NV) are displayed to be overlaid on the image information based on the fundus image.

Next, a flow of a series of processes executed by the server 1 having the functional configuration of FIG. 3 will be described with reference to FIG. 4.

Figure 4:
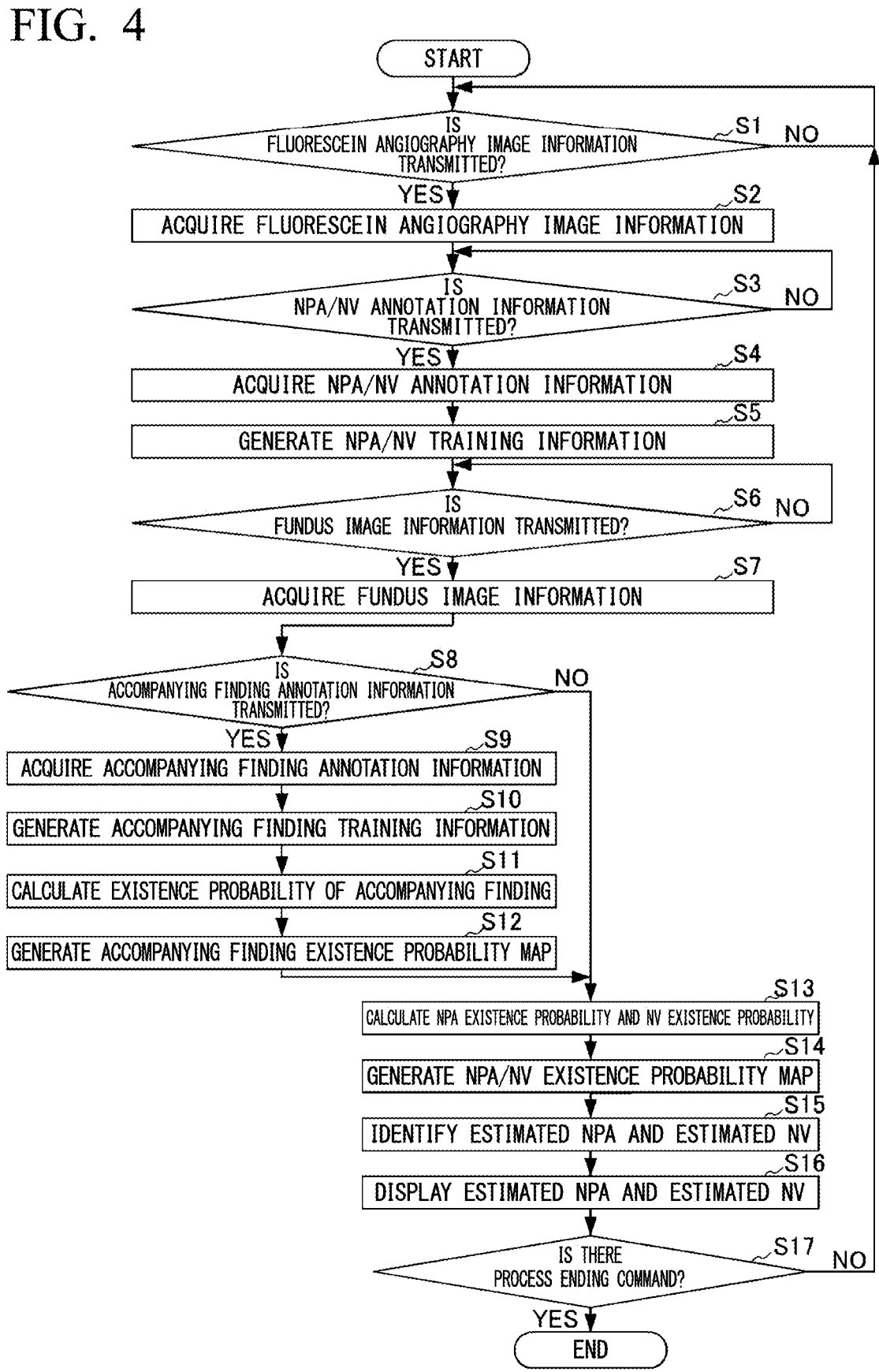
FIG. 4 is a flowchart illustrating a flow of various processes such as the NPA/NV existence probability map generating process, the accompanying finding existence probability map generating process, the estimated NPA/NV recognizing process, and the estimated NPA/NV display process executed by the server shown in FIG. 3.

FIG. 4 is a flowchart illustrating a flow of a series of processes executed by the server 1 of FIG. 3.

As shown in FIG. 4, the server 1 executes the following series of processes.

In step S1, the image acquisition unit 101 determines whether or not fluorescein angiography image information has been transmitted from the examination device 3.

In a case where the fluorescein angiography image information has been transmitted, the determination in step S1 is affirmative, and the procedure proceeds to step S2. On the other hand, in a case where the fluorescein angiography image information has not been transmitted, the determination in step S1 is negative, and the procedure returns to step S1. That is, the determination process of step S1 is repeated until the fluorescein angiography image information is transmitted. Thereafter, in a case where the fluorescein angiography image information is transmitted, the determination in step S1 becomes affirmative, and the procedure proceeds to step S2.

In step S2, the image acquisition unit 101 acquires the transmitted fluorescein angiography image information.

In step S3, the annotation acquisition unit 102 determines whether or not NPA/NV annotation information has been transmitted from the ophthalmologist terminal 2.

In a case where the NPA/NV annotation information has been transmitted, the determination in step S3 is affirmative, and the procedure proceeds to step S4. On the other hand, in a case where the NPA/NV annotation information has not been transmitted, the determination in step S3 is negative, and the procedure returns to step S3. That is, the determination process of step S3 is repeated until the NPA/NV annotation information is transmitted. Thereafter, in a case where the NPA/NV annotation information is transmitted, the determination in step S3 becomes affirmative, and the procedure proceeds to step S4.

In step S4, the annotation acquisition unit 102 acquires the transmitted NPA/NV annotation information.

In step S5, the training information generation unit 103 generates NPA/NV training information on the basis of the fluorescein angiography image information and the NPA/NV annotation information corresponding to the fluorescein angiography image information.

In step S6, the image acquisition unit 101 determines whether or not fundus image information has been transmitted from the examination device 3.

In a case where the fundus image information has been transmitted, the determination in step S6 is affirmative, and the procedure proceeds to step S7. On the other hand, in a case where the fundus image information has not been transmitted, the determination in step S6 is negative, and the procedure returns to step S6. That is, the determination process of step S6 is repeated until the fundus image information is transmitted. Thereafter, in a case where the fundus image information is transmitted, the determination in step S6 becomes affirmative, and the procedure proceeds to step S7.

In step S7, the image acquisition unit 101 acquires the transmitted fundus image information.

In step S8, the annotation acquisition unit 102 determines whether or not accompanying finding annotation information has been transmitted from the ophthalmologist terminal 2.

In a case where the accompanying finding annotation information has been transmitted, the determination in step S8 is affirmative, and the procedure proceeds to Step S9. On the other hand, in a case where the accompanying finding annotation information has not been transmitted, the determination in step S8 is negative, and the procedure skips steps S9 to S11 and proceeds to step S12.

In step S9, the annotation acquisition unit 102 acquires the accompanying finding annotation information.

In step S10, the training information generation unit 103 generates the accompanying finding training information on the basis of the fluorescein angiography image information and the NPA/NV annotation information corresponding to the fluorescein angiography image information.

In step S11, the arithmetic unit 104 calculates an existence probability of an accompanying finding in the fundus image information on the basis of the accompanying finding training information.

In step S12, the map generation unit 105 generates an accompanying finding existence probability map as image information in which the accompanying finding existence probability is identifiably displayed in the fundus image information.

In step S13, the arithmetic unit 104 calculates the NPA existence probability and the NV existence probability on the basis of at least the NPA/NV training information. Further, in a case where the accompanying finding existence probability map is generated, the arithmetic unit 104 calculates the NPA existence probability and the NV existence probability on the basis of the NPA/NV training information and the accompanying finding existence probability map.

In step S14, the map generation unit 105 generates an NPA/NV existence probability map as image information in which the NPA existence probability and the NV existence probability are identifiably displayed in the fundus image information.

In step S15, the estimated NPA/NV identification unit 106 identifies an area that is estimated to correspond to the retinal non-perfusion area (NPA) in the fundus image information, as an estimated NPA, and identifies an area that is estimated to correspond to the neovascularization (NV), as an estimated NV, on the basis of the NPA existence probability and the NV existence probability.

In step S16, the estimated NPA/NV display control unit 107 executes a control for displaying the estimated NPA and the NV area on the fundus image information.

In step S17, the server 1 determines whether or not there is a process ending command.

In a case where there is no process ending command, the determination in step S17 is negative, and the procedure returns to step S1. On the other hand, in a case where there is the process ending command, the determination in step S17 is affirmative, and the procedure ends.

In a case where the server 1 executes the series of processes described above, the estimated NPA area and the estimated NV area are displayed in the fundus image information.

Next, a flow of various types of information used in various types of processes executed by the server 1 will be described with reference to FIG. 5.

Figure 5:
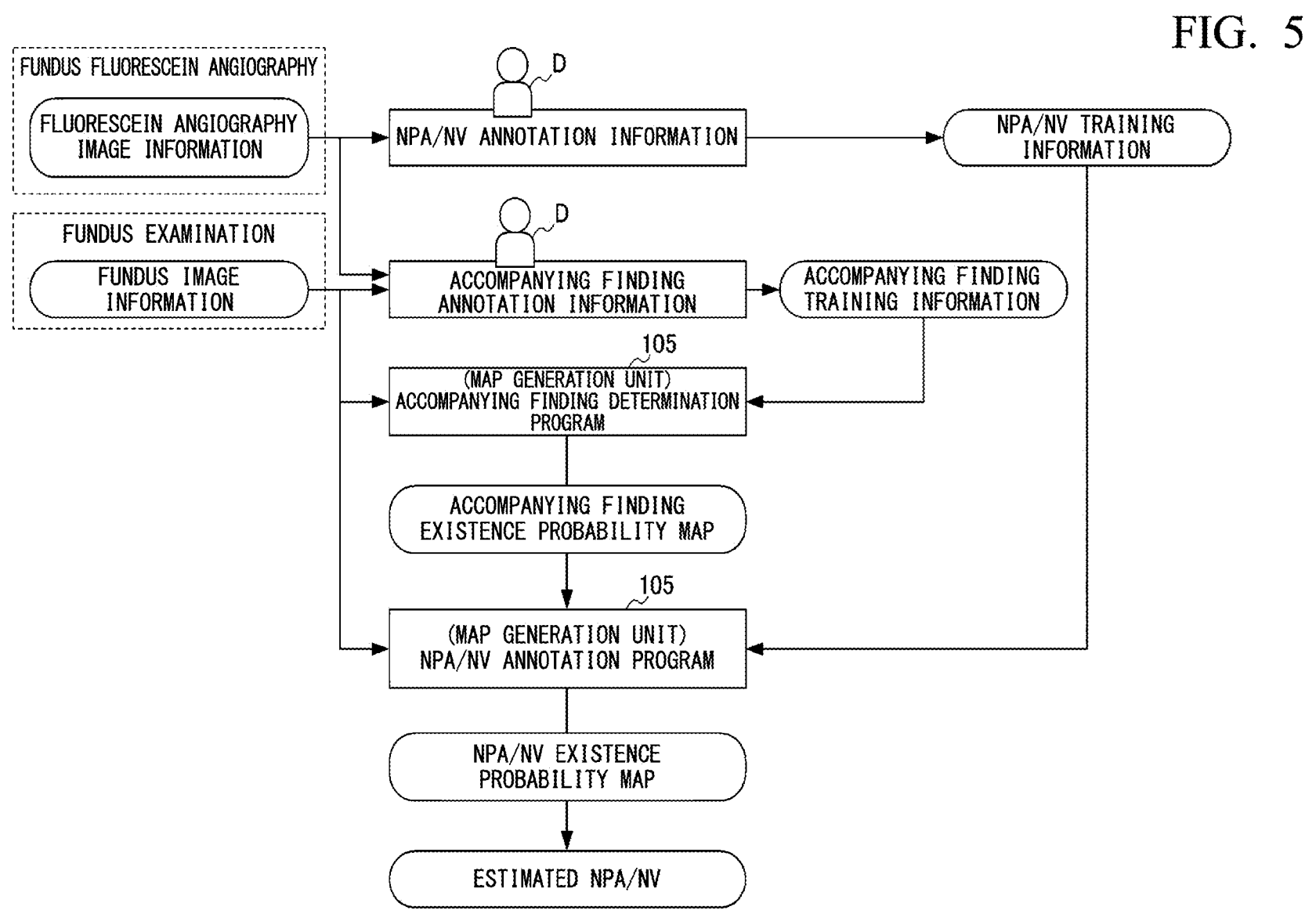

FIG. 5 is a diagram illustrating a flow of various types of information in the processes executed by the server 1.

As shown in FIG. 5, in a case where a fluorescein angiography image of a patient is captured in fundus fluorescein angiography, the server 1 acquires fluorescein angiography image information based on the fluorescein angiography image. A diagnostic note of the ophthalmologist D regarding at least one of the retinal non-perfusion area (NPA) or the neovascularization (NV) is attached to this fluorescein angiography image information. The diagnostic note forms the NPA/NV training information together with the fluorescein angiography image information as the NPA/NV annotation information.

In a case where a fundus image of a patient is captured in a fundus examination, fundus image information based on the fundus image is acquired by the server 1. The fundus image information and the NPA/NV training information are used for a calculation process based on a NPA/NV annotation program of the arithmetic unit 104. As a result of the calculation process based on the NPA/NV annotation program, an NPA/NV existence probability map is generated. An estimated NPA and an estimated NV in the fundus image information are identified on the basis of the NPA/NV existence probability map.

A diagnostic note of the ophthalmologist D regarding an accompanying finding may be attached to the fluorescein angiography image information and the fundus image information. The diagnostic note in this case forms the accompanying finding training information together with the fluorescein angiography image information and the fundus image information as the accompanying finding annotation information.

The fundus image information and the NPA/NV training information are used for a calculation process based on an accompanying finding determination program of the arithmetic unit 104. As a result of the calculation process based on the accompanying finding determination program, an accompanying finding existence probability map is generated. In this manner, in a case where the accompanying finding existence probability map is generated, the estimated NPA and the estimated NV in the fundus image information are identified on the basis of the accompanying finding existence probability map and the NPA/NV training information.

Figure 6:
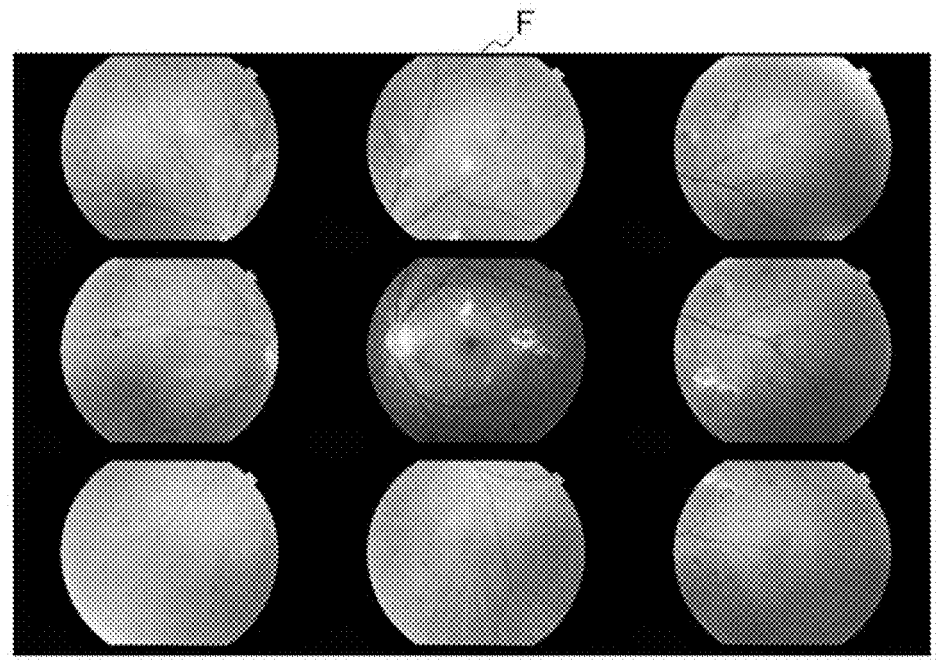
FIG. 6 is a diagram illustrating an example of fundus image information acquired in the processes executed by the server shown in FIG. 3.

FIG. 6 is a diagram illustrating an example of fundus image information acquired in the process executed by the server 1.

Figure 7:
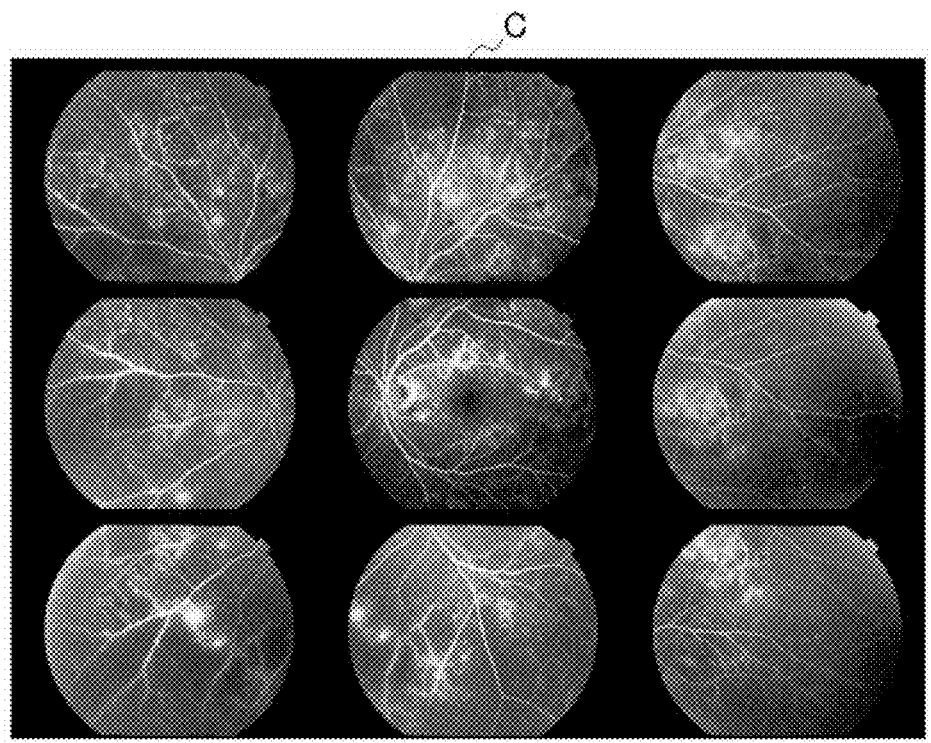
FIG. 7 is a diagram illustrating an example of fluorescein angiography image information acquired in the processes executed by the server shown in FIG. 3.

FIG. 7 is a diagram illustrating an example of fluorescein angiography image information acquired in the process executed by the server 1.

In examination of the fundus of a patient, imaging of the fundus of the patient is performed by the examination device 3, and accordingly, fundus image information as shown in FIG. 6 is obtained. The ophthalmologist D performs diagnosis with reference to the fundus image information as shown in FIG. 6. However, as shown in FIG. 6, the fundus image information only shows findings resulting from abnormal perfusion such as bleeding and vitiligo, and it is difficult to read circulatory dynamics and an abnormal circulatory site. Therefore, fundus fluorescein angiography is performed, and accordingly, fluorescein angiography image information as shown in FIG. 7 is obtained. As shown in FIG. 7, retinal circulatory dynamics can be clearly discriminated from the fluorescein angiography image information. However, the fundus fluorescein angiography is a burdensome examination for both patients and medical staffs due to the risk of the examination, its invasiveness, and geographical restrictions such as limitation to large hospitals, which causes hesitancy to take pictures of patients with good eyesight, patients with reduced physical functions, to perform repeated imaging, or the like, and thus, there are many cases in that detection of symptom appearances or disease states is delayed and treatment is delayed.

Accordingly, the server 1 performs an NPA/NV existence probability map generating process using the stored fluorescein angiography image information obtained from a plurality of patients and the NPA/NV training information generated on the basis of the NPA/NV annotation information attached to each piece of fluorescein angiography image information. Thus, it is possible to easily recognize abnormal circulatory findings from fundus images that can be easily captured at a nearby clinic or medical examination without performing the burdensome fundus fluorescein angiography.

FIG. 8 is a diagram illustrating an example of the NPA/NV existence probability map output in the NPA/NV existence probability map generating process executed by the server 1.

An NPA/NV existence probability map E shown in FIG. 8 is image information in which the NPA existence probability and the NV existence probability are identifiably displayed in the fundus image information. In the NPA/NV existence probability map E, the NPA existence probability and the NV existence probability may be identifiably displayed according to color differences or color shades. For example, the identification display may be performed in such a manner that an area indicated by a warm color has a high NPA existence probability and a high NV existence probability and an area indicated by a cold color has a low NPA existence probability and a low NV existence probability. In addition, even in an area indicated by a cold color having a low NPA existence probability and a low NV existence probability, the identification display may be performed in such a manner that a dark color area has a lower NPA existence probability and a lower NV existence probability than a light color area.

Thus, it is possible to generate information that serves as a basis for estimating the existence of the retinal non-perfusion area (NPA) and the neovascularization (NV) in the fundus image information.

Figure 9:
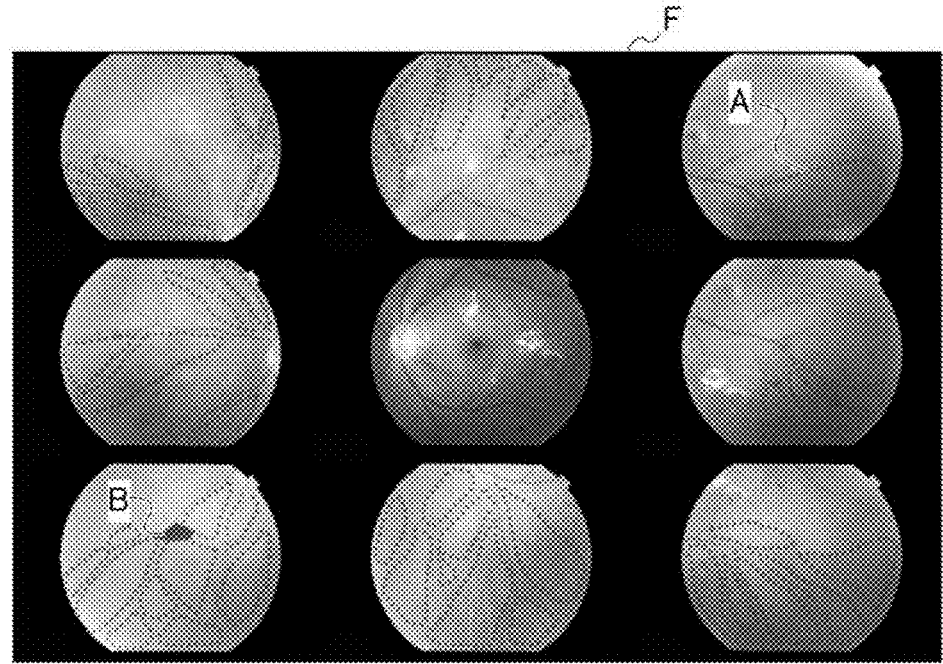
FIG. 9 is a diagram illustrating an estimated NPA and an estimated NV identified in the estimated NPA/NV recognizing process executed by the server shown in FIG. 3.

FIG. 9 is a diagram illustrating an example of an estimated NPA and an estimated NV identified in the estimated NPA/NV recognizing process executed by the server 1.

On the basis of the content of the NPA/NV existence probability map, the server 1 identifies an area of the fundus image information that is estimated to correspond to the retinal non-perfusion area (NPA), as an estimated NPA, and identifies an area that is estimated to correspond to the neovascularization (NV), as an estimated NV. For example, as shown in FIG. 9, an area A indicated by a broken line may be set as the estimated NPA, and an area B may be set as the estimated NV. The estimated NPA and the estimated NV may be displayed to be superimposed on the fundus image information.

Thus, it is possible to quickly and easily identify an area in which the existence of a retinal non-perfusion is estimated and an area where the existence of a neovascularization is estimated, from a fundus image obtained by imaging the fundus of a patient, without performing the fundus fluorescein angiography that requires a special fundus camera or a diagnosis device.

One embodiment of the present invention has been described above, but the present invention is not limited to the above-described embodiment, and modifications, improvements, or the like within a range in which the object of the present invention can be achieved are included in the present invention.

For example, in the above-described embodiment, a configuration in which the image acquisition unit 101 acquires, in a case where various types of image information are transmitted from the examination device 3, the various types of image information is shown, but a configuration in which the image acquisition unit 101 voluntarily goes to obtain various types of image information in a case where imaging is performed by the examination device 3 may be used. Similarly, a configuration in which the annotation acquisition unit 102 acquires, in a case where various types of annotation information are transmitted from the ophthalmologist terminal 2, the various types of annotation information is shown, but a configuration in which in a case where the various types of annotation information is input to the ophthalmologist terminal 2, the annotation acquisition unit 102 voluntarily goes to obtain the various types of annotation information may be used.

The hardware configurations shown in FIG. 2 are merely examples for achieving the object of the present invention, and are not particularly limited.

The functional block diagram shown in FIG. 3 is merely an example, and is not particularly limited. That is, it is sufficient if the information processing system has functions capable of executing the above-described series of processes as a whole, and what kind of functional block is used to realize the function is not particularly limited to the example of FIG. 3.

Further, existence locations of the functional blocks are not limited to locations shown in FIG. 3, and may be appropriately modified. For example, at least a part of the functional blocks of the server 1 may be provided in the ophthalmologist terminal 2 or the examination device 3.

Then, one functional block may be configured by a hardware unit, or may be configured by a combination with a software unit.

In a case where the processing of each functional block is executed by software, a program that forms the software is installed in a computer or the like from a network or a recording medium.

The computer may be a computer embedded in dedicated hardware. In addition, the computer may be a computer capable of executing various functions by installation of various programs, for example, a general-purpose smartphone or a personal computer as well as a server.

The recording medium that stores such a program is not only configured by a removable medium that is distributed separately from a device body in order to provide the program to each user, but is also configured by a recording medium or the like provided to each user in a state of being incorporated in the device body in advance.

In the present specification, steps of describing the program recorded on the recording medium are not only processes sequentially performed in a time series manner, but may also include processes performed in parallel or individually although the processes are not necessarily performed in a time series manner.

For example, in step S6 of FIG. 4, the image acquisition unit 101 determines whether or not the fundus image information has been transmitted from the examination device 3, and acquires the fundus image information in step S7. However, in a case where the accompanying finding existence probability map generating process is executed, the fundus image information has only to be appropriately managed at a time point when the accompanying finding training information is generated. Further, in a case where the accompanying finding existence probability map generating process is not executed, the fundus image information has only to be appropriately managed at a time point when the NPA existence probability and the NV existence probability are calculated. Accordingly, in a case where the accompanying finding training information is generated, the fundus image information may be stored for management in the image DB 401 from any time point before the accompanying finding training information is generated in step S10. Further, in a case where the accompanying finding training information is not generated, the fundus image information may be stored for management in the image DB 401 from any time point before the NPA existence probability and the NV existence probability are calculated in step S13.

In summary, a program to which the present invention is applied may have the following configuration, and may have various embodiments.

That is, the program to which the present invention is applied causes a computer that controls the information processing device to execute: a fluorescein angiography image acquisition step (for example, step S2 in FIG. 4) of acquiring fluorescein angiography image information (for example, fluorescein angiography image information C in FIG. 7); an NPA/NV annotation acquisition step (for example, step S4 in FIG. 4) of acquiring a diagnostic note of an ophthalmologist regarding at least one of a retinal non-perfusion area (NPA) or a neovascularization (NV), attached to the fluorescein angiography image information, as NPA/NV annotation information; an NPA/NV training information generation step (for example, step S5 in FIG. 4) of generating NPA/NV training information that is training information for calculating an existence probability of the retinal non-perfusion area (NPA) and an existence probability of the neovascularization (NV), on the basis of the fluorescein angiography image information and the NPA/NV annotation information corresponding to the fluorescein angiography image information; a fundus image acquisition step (for example, step S7 in FIG. 4) of acquiring fundus image information (for example, fundus image information F in FIG. 6); an NPA/NV existence probability calculation step (for example, step S13 in FIG. 4) of calculating the existence probability of the retinal non-perfusion area (NPA) and the existence probability of the neovascularization (NV) in the fundus image information on the basis of the NPA/NV training information; and an estimated NPA/NV identification step (for example, step S15 in FIG. 4) of recognizing an area of the fundus image information that is estimated to correspond to the retinal non-perfusion area (NPA), as an estimated NPA, and recognizing an area that is estimated to correspond to the neovascularization (NV), as an estimated NV, on the basis of the existence probability of the retinal non-perfusion area and the existence probability of the neovascularization.

Thus, it is possible to quickly and easily identify the area in which the existence of retinal non-perfusion is estimated from the fundus image obtained by imaging the fundus of a patient, without performing fundus fluorescein angiography that requires a special fundus camera or a diagnosis device.

In addition, the program may cause the computer to execute the control process further including: an NPA/NV existence probability map generation step (for example, step S14 in FIG. 4) of generating an NPA/NV existence probability map (for example, the NPA/NV existence probability map E in FIG. 8) in which the NPA existence probability and the NV existence probability are identifiably displayed in the fundus image information.

Thus, it is possible to generate information that serves as a basis for estimating the existence of the retinal non-perfusion area (NPA) and the neovascularization (NV) in the fundus image information.

In addition, the program may cause the computer to further execute: an accompanying annotation acquisition step (for example, step S9 in FIG. 4) of acquiring, as accompanying finding annotation information, a diagnostic note of the ophthalmologist regarding an accompanying finding, attached to the fluorescein angiography image information and the fundus image information; an accompanying finding training information generation step (for example, step S10 in FIG. 4) of generating accompanying finding training information that serves as training information for calculating an existence probability of the accompanying finding in the fundus image information, on the basis of the fluorescein angiography image information and the fundus image information, and the accompanying finding annotation information corresponding to the fluorescein angiography image information and the fundus image information; and an accompanying finding existence probability calculation step (for example, step S11 in FIG. 4) of calculating the existence probability of the accompanying finding in the fundus image information on the basis of the accompanying finding training information, and in the NPA/NV existence probability calculation step, a control process of calculating the existence probability of the retinal non-perfusion area (NPA) and the existence probability of the neovascularization (NV) in the fundus image information on the basis of the accompanying finding existence probability and the NPA/NV training information may be executed.

Further, the program may cause the computer to further execute: an accompanying finding existence probability map generation step (for example, step S12 in FIG. 4) of generating an accompanying finding existence probability map in which the existence probability of the accompanying finding is identifiably displayed in the fundus image information.

Hereinafter, a modified example of the embodiment of the present invention will be described with reference to the drawings.

Modified Example

Figure 10:
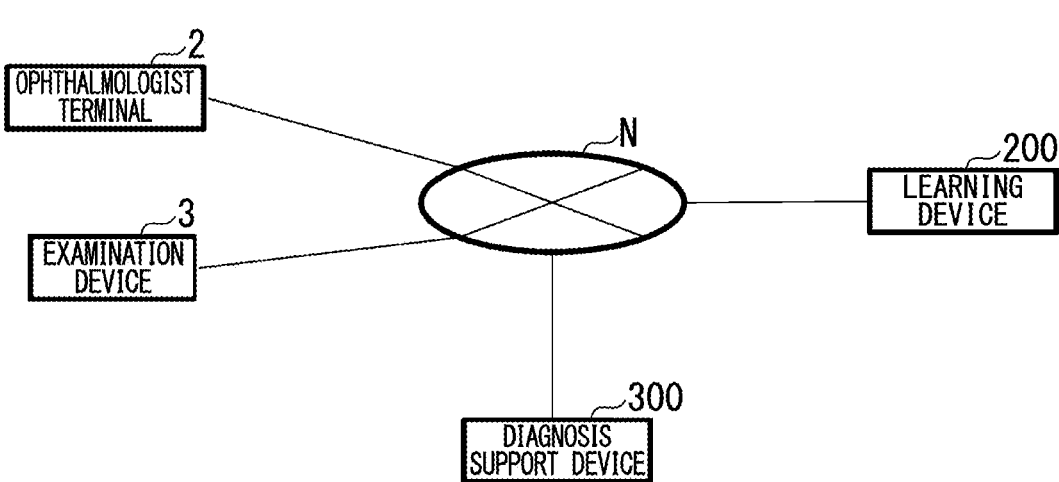
FIG. 10 is a configuration diagram illustrating an information processing system according to a modified example of the embodiment of the present invention.

FIG. 10 is a configuration diagram of an information processing system of a modified example according to the embodiment of the present invention. The information processing system of the modified example according to the embodiment of the present invention includes the ophthalmologist terminal 2, the examination device 3, a learning device 200, and a diagnosis support device 300. These devices are connected to each other through a network N.

The learning device 200 generates, on the basis of a fundus image that is an image of the fundus and an area of abnormality in blood circulation specified on the basis of a fluorescein angiography image of the fundus, a trained model indicating a relationship between the fundus image and the area of abnormality in blood circulation in the fundus image through learning. Here, the area of abnormality in blood circulation is an area in which blood circulation is abnormal due to blood damage on the retina that occurs in ocular ischemic diseases such as diabetic retinopathy.

The learning device 200 acquires information indicating a fundus image of a patient and information indicating a fluorescein angiography image of the patient, and stores the information indicating the fundus image and the information indicating the fluorescein angiography image acquired above in association with each other. Specifically, in a fundus examination of a patient, the examination device 3 captures a fundus image of the patient, creates fundus image notification information including a patient ID and information indicating the captured fundus image, to be addressed to the learning device 200, and transmits the created fundus image notification information to the learning device 200. In addition, in the fundus fluorescein angiography of the patient, the examination device 3 captures a fluorescein angiography image of the patient, creates fluorescein angiography image notification information including the patient ID and information indicating the captured fluorescein angiography image, to be addressed to the learning device 200, and transmits the created fluorescein angiography image notification information to the learning device 200.

The learning device 200 acquires the patient ID and the information indicating the fundus image included in the fundus image notification information transmitted from the examination device 3 to the learning device 200, the patient ID and the information indicating the fluorescein angiography image included in the fluorescein angiography image notification information, and stores the patient ID, the information indicating the fundus image, and the information indicating the fluorescein angiography image acquired above in association with each other.

The learning device 200 acquires a diagnostic note of the ophthalmologist D regarding any one or both of the retinal non-perfusion area (NPA) and the neovascularization (NV), attached to the fluorescein angiography image of the patient, as NPA/NV annotation information. Specifically, in the fundus fluorescein angiography, in a case where the diagnostic note of the ophthalmologist D regarding the retinal non-perfusion area (NPA) and the neovascularization (NV) is attached to the fluorescein angiography image, the ophthalmologist terminal 2 creates NPA/NV annotation notification information including the patient ID and the diagnostic note, to be addressed to the learning device 200, on the basis of an operation of the ophthalmologist D, and transmits the created NPA/NV annotation notification information to the learning device 200.

The learning device 200 receives the NPA/NV annotation notification information transmitted by the ophthalmologist terminal 2, and stores the NPA/NV annotation information included in the received NPA/NV annotation notification information. The information indicating the fluorescein angiography image and the NPA/NV annotation information attached to the fluorescein angiography image are stored in association with each other.

The learning device 200 acquires a diagnostic note of the ophthalmologist D regarding the accompanying finding, attached to the fundus image and the fluorescein angiography image, as accompanying finding annotation information. Specifically, in a case where the diagnostic note of the ophthalmologist D regarding the accompanying findings is attached to the information indicating the fluorescein angiography image and the information indicating the fundus image, the ophthalmologist terminal 2 creates accompanying finding annotation notification information including the patient ID and the diagnostic note, to be addressed to the learning device 200, on the basis of an operation of the ophthalmologist D, and transmits the created accompanying finding annotation notification information to the learning device 200. The learning device 200 receives the accompanying finding annotation notification information transmitted by the ophthalmologist terminal 2, acquires the patient ID and the accompanying finding annotation information included in the received accompanying finding annotation notification information, and stores the acquired patient ID and the accompanying finding annotation information. The information indicating the fundus image, the information indicating the fluorescein angiography image, and the accompanying finding annotation information are stored in association with each other.

The learning device 200 acquires the information indicating the fundus image, the information indicating the fluorescein angiography image associated with the information indicating the fundus image, the NPA/NV annotation information, and the accompanying finding annotation information, and specifies an area of abnormality in blood circulation on the basis of the information indicating the fluorescein angiography image, the NPA/NV annotation information, and the accompanying finding annotation information acquired above. The learning device 200 generates NPA/NV learning information in which the information correlating the fundus image and the area of abnormality in blood circulation specified on the basis of the fluorescein angiography image corresponding to the fundus image, and stores the generated NPA/NV learning information.

The learning device 200 generates, using the information indicating the fundus image included in the NPA/NV learning information as input information, and using the area of abnormality in blood circulation specified on the basis of the fluorescein angiography image corresponding to the fundus image as training information, a trained model indicating a relationship between the fundus image and the area of abnormality in blood circulation in the fundus image through learning. A specific method of generating the trained model is not particularly limited. For example, a method for extracting a feature common in the fundus images having the area of abnormality in blood circulation from the NPA/NV learning information, and deriving a relationship between the extracted common feature and the area of abnormality in blood circulation in the fundus image may be used. The relationship between the fundus image and the area of abnormality in blood circulation in the fundus image may be derived using a neural network or a deep learning technique. The learning device 200 stores the generated trained model, creates trained model notification information including the trained model, to be addressed to the diagnosis support device 300, and transmits the created trained model notification information to the diagnosis support device 300.

The diagnosis support device 300 receives the trained model transmitted by the learning device 200, and stores the received trained model.

The ophthalmologist terminal 2 creates patient information including the patient ID and the information indicating the fundus image of the patient, to be addressed to the diagnosis support device 300, and transmits the created patient information to the diagnosis support device 300.

The diagnosis support device 300 receives the patient information transmitted by the ophthalmologist terminal 2, and acquires the patient ID and the information indicating the fundus image of the patient included in the received patient information. The diagnosis support device 300 specifies the area of abnormality in blood circulation in the fundus image on the basis of the acquired information indicating the fundus image, using the stored trained model. The diagnosis support device 300 creates a diagnosis result including the information indicating an area of abnormality in blood circulation in the fundus image identified using the patient fundus image and the trained model and the patient ID, to be addressed to the ophthalmologist terminal 2, and transmits the created diagnosis result to the ophthalmologist terminal 2.

Hereinafter, the learning device 200 and the diagnosis support device 300 included in the information processing system will be described.

(Learning Device 200)

Figure 11:
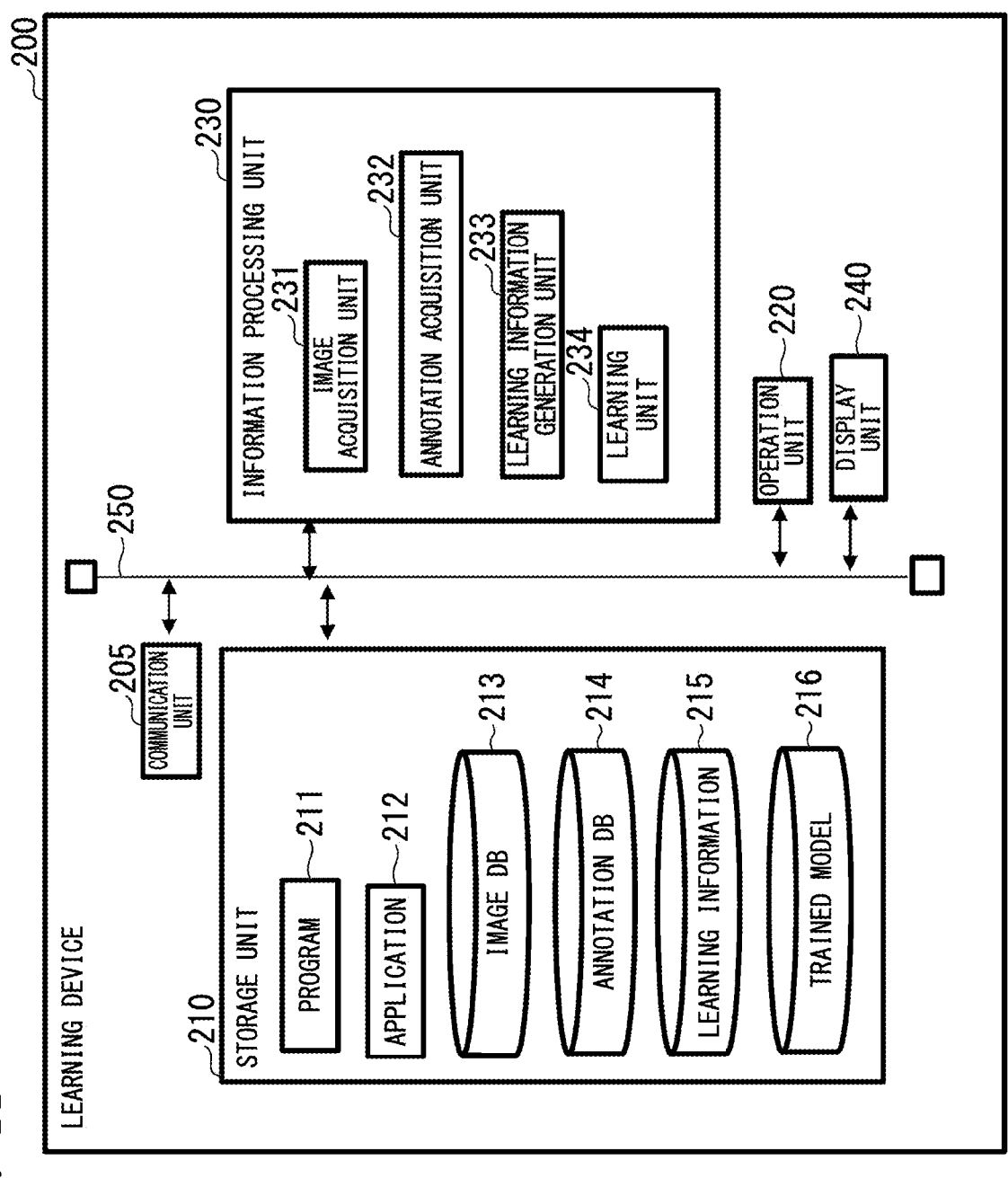
FIG. 11 is a block diagram illustrating an example of a learning device according to a modified example of the embodiment of the present invention.

FIG. 11 is a block diagram illustrating an example of a learning device according to a modified example of the embodiment of the present invention.

The learning device 200 includes a communication unit 205, a storage unit 210, an operation unit 220, an information processing unit 230, a display unit 240, and a bus line 250 such as an address bus or a data bus for electrically connecting the respective components as shown in FIG. 11.

The communication unit 205 is realized by a communication module. The communication unit 205 communicates with external communication devices such as the ophthalmologist terminal 2, the examination device 3, or the diagnosis support device 300 through the network N. Specifically, the communication unit 205 receives fundus image notification information transmitted by the examination device 3, and outputs the received fundus image notification information to the information processing unit 230. The communication unit 205 receives fluorescein angiography image notification information transmitted by the examination device 3, and outputs the received fluorescein angiography image notification information to the information processing unit 230. The communication unit 205 receives NPA/NV annotation notification information transmitted by the ophthalmologist terminal 2, and outputs the received NPA/NV annotation notification information to the information processing unit 230. The communication unit 205 receives accompanying finding annotation notification information transmitted by the ophthalmologist terminal 2, and outputs the received accompanying finding annotation notification information to the information processing unit 230. The communication unit 205 acquires trained model notification information output by the information processing unit 230, and transmits the acquired trained model notification information to the diagnosis support device 300.

The storage unit 210 is realized by, for example, a random access memory (RAM), a read only memory (ROM), a hard disk drive (HDD), a flash memory, or a hybrid storage device in which a plurality of these memories are combined. The storage unit 210 stores a program 211 executed by the information processing unit 230, an application 212, an image DB 213, an annotation DB 214, learning information storage 215, and a trained model 216.

The program 211 is, for example, an operating system, which is located between a user or an application program and hardware, provides a standard interface for the user or the application program, and performs efficient management for each resource such as hardware.

The application 212 causes the learning device 200 to receive the fundus image notification information transmitted by the examination device 3, and to store the patient ID and the information indicating the fundus image included in the received fundus image notification information in association with each other. The application 212 causes the learning device 200 to receive the fluorescein angiography image notification information transmitted by the examination device 3, and to store the patient ID and the information indicating the fluorescein angiography image included in the received fluorescein angiography image notification information in association with each other. The application 212 causes the learning device 200 to receive the NPA/NV annotation notification information transmitted by the ophthalmologist terminal 2, and to store the patient ID and the NPA/NV annotation information included in the received NPA/NV annotation notification information in association with each other.

The application 212 causes the learning device 200 to receive the accompanying finding annotation notification information transmitted by the ophthalmologist terminal 2, and to store the patient ID and the accompanying finding annotation information included in the received accompanying finding annotation notification information in association with each other. The application 212 causes the learning device 200 to acquire the information indicating the fundus image, the information indicating the fluorescein angiography image, the NPA/NV annotation information, and the accompanying finding annotation information associated with the patient ID. The application 212 causes the learning device 200 to specify the area of abnormality in blood circulation on the basis of the information indicating the fluorescein angiography image, the NPA/NV annotation information, and the accompanying finding annotation information acquired above.

The application 212 causes the learning device 200 to generate NPA/NV learning information in which the information indicating the fundus image and the area of abnormality in blood circulation specified on the basis of the fluorescein angiography image corresponding to the fundus image are associated with each other, and to store the generated NPA/NV learning information. The application 212 causes the learning device 200 to generate, using the information indicating the fundus image included in the NPA/NV learning information as input information, and using the area of abnormality in blood circulation specified on the basis of the fluorescein angiography image corresponding to the fundus image as training information, a trained model indicating a relationship between the fundus image and the area of abnormality in blood circulation in the fundus image through learning. The application 212 causes the learning device 200 to store the generated trained model, and to transmit the trained model to the diagnosis support device 300.

The image DB 213 stores the patient ID, the information indicating the fundus image, and the information indicating the fluorescein angiography image in association with each other.

The annotation DB 214 stores the patient ID, the NPA/NV annotation information, and the accompanying finding annotation information in association with each other.

The learning information storage 215 stores the NPA/NV learning information in which the information indicating the fundus image and the area of abnormality in blood circulation specified on the basis of the fluorescein angiography image corresponding to the fundus image in association with each other.

The trained model 216 stores, using the information indicating the fundus image included in the NPA/NV learning information as input information, and using the area of abnormality in blood circulation specified on the basis of the fluorescein angiography image corresponding to the fundus image as training information, the trained model indicating the relationship between the fundus image and the area of abnormality in blood circulation in the fundus image.

The operation unit 220 is configured by, for example, a touch panel, which detects a touch operation on a screen displayed on the display unit 240, and outputs a detection result of the touch operation to the information processing unit 230.

The display unit 240 is configured by, for example, a touch panel, which displays a screen for receiving the information indicating the fundus image received by the learning device 200 and the information indicating the fluorescein angiography image. Further, the display unit 240 displays a screen for receiving an operation of processing the NPA/NV annotation information received by the learning device 200 and the accompanying finding annotation information.

The entirety or a part of the information processing unit 230 is, for example, a function unit (hereinafter, referred to as a software function unit) realized as a processor such as a central processing unit (CPU) executes the program 211 stored in the storage unit 210 and the application 212. The entirety or a part of the information processing unit 230 may be realized by hardware such as a large scale integration (LSI), an application specific integrated circuit (ASIC), or a field-programmable gate array (FPGA), or may be realized by a combination of a software function unit and hardware. The information processing unit 230 includes, for example, an image acquisition unit 231, an annotation acquisition unit 232, a learning information generation unit 233, and a learning unit 234.

The image acquisition unit 231 acquires the fundus image notification information output by the communication unit 205, and acquires the patient ID and the information indicating the fundus image included in the acquired fundus image notification information. The image acquisition unit 231 stores the patient ID and the information indicating the fundus image acquired above in association with each other in the image DB 213.

The image acquisition unit 231 acquires the fluorescein angiography image notification information output by the communication unit 205, and acquires the patient ID and the information indicating the fluorescein angiography image included in the acquired fluorescein angiography image notification information. The image acquisition unit 231 stores the patient ID and the information indicating the fluorescein angiography image acquired above in association with each other in the image DB 213.

The annotation acquisition unit 232 acquires the NPA/NV annotation notification information output by the communication unit 205, and acquires the patient ID and the NPA/NV annotation information included in the acquired NPA/NV annotation notification information. The annotation acquisition unit 232 stores the patient ID and the NPA/NV annotation information acquired above in association with each other in the annotation DB 214.

The annotation acquisition unit 232 acquires the accompanying finding annotation notification information output by the communication unit 205, and acquires the patient ID and the accompanying finding annotation information included in the acquired accompanying finding annotation notification information. The annotation acquisition unit 232 stores the patient ID and the accompanying finding annotation information acquired above in association with each other in the annotation DB 214.

The learning information generation unit 233 acquires the patient ID, the information indicating the fundus image associated with the patient ID, and the information indicating the fluorescein angiography image stored in the image DB 213 of the storage unit 210. The learning information generation unit 233 acquires the patient ID, the NPA/NV annotation information associated with the patient ID, and the accompanying finding annotation information stored in the annotation DB 214 of the storage unit 210. The learning information generation unit 233 specifies the area of abnormality in blood circulation on the basis of the information indicating the fluorescein angiography image, the NPA/NV annotation information, and the accompanying finding annotation information acquired above.

Hereinafter, each configuration of the learning device 200 will be specifically described.

Figure 12:
FIG. 12 is a diagram illustrating an example of a fundus image.
Figure 13:
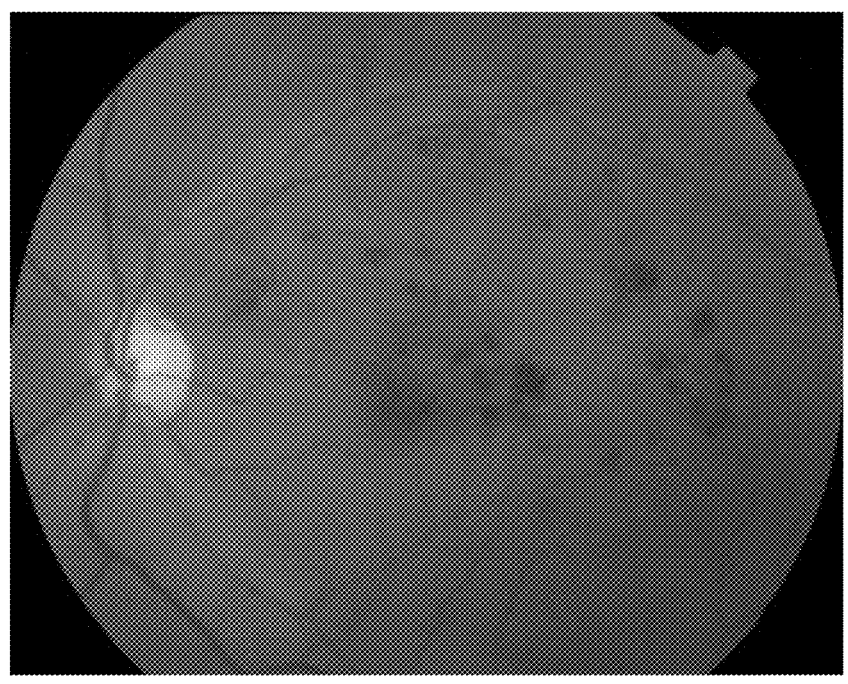
FIG. 13 is a diagram illustrating an example of a fluorescein angiography image.

FIG. 12 is a diagram illustrating an example of a fundus image, and FIG. 13 is a diagram illustrating an example of a fluorescein angiography image.

The learning information generation unit 233 extracts a green component of the fundus image, and removes a noise component from a green component extraction fundus image that is a fundus image obtained by the extraction of the green component. The learning information generation unit 233 divides the green component extraction fundus image from which the noise component is removed into rectangles. The learning information generation unit 233 resizes the green component extraction fundus image from which the noise component is removed to a predetermined size on the basis of the image divided into rectangles. In resizing the green component extraction fundus image into the predetermined size, interpolation is performed by an interpolation method such as bicubic interpolation.

The learning information generation unit 233 extracts a green component of the fluorescein angiography image, and removes a noise component from a green component extraction fluorescein angiography image which is a fluorescein angiography image obtained by the extraction of the green component. The learning information generation unit 233 divides the green component extraction fluorescein angiography image from which the noise component is removed into rectangles. The learning information generation unit 233 resizes the green component extraction fluorescein angiography image from which the noise component is removed to a predetermined size on the basis of the image divided into rectangles. In resizing the green component extraction fluorescein angiography image into the predetermined size, interpolation is performed by an interpolation method such as bicubic interpolation.

The learning information generation unit 233 corrects rotational components of the green component extraction fundus image from which the noise component is removed and the green component extraction fluorescein angiography image from which the noise component is removed so that positions of eyeballs coincide with each other, and performs resizing to a predetermined size. The learning information generation unit 233 corrects the rotational components so that the positions of the eyeballs coincide with each other, and specifies an area of abnormality in blood circulation on the basis of the green component extraction fundus image from which the noise component is removed and the green component extraction fluorescein angiography image from which the noise component is removed, resized to the predetermined size.

Figure 14:
FIG. 14 is a diagram illustrating an example of an area of abnormality in blood circulation.

FIG. 14 is a diagram illustrating an example of an area of abnormality in blood circulation.

The learning information generation unit 233 generates NPA/NV learning information in which the information indicating the fundus image and the area of abnormality in blood circulation specified on the basis of the fluorescein angiography image corresponding to the fundus image are associated with each other, and stores the generated NPA/NV learning information in the learning information storage 215 of the storage unit 210. Returning to FIG. 11, the description will be continued.

The learning unit 234 acquires the NPA/NV learning information stored in the learning information storage 215 of the storage unit 210. The learning unit 234 acquires information indicating the fundus image and the information indicating the area of abnormality in blood circulation included in the acquired NPA/NV learning information. The learning unit 234 generates, using the acquired information indicating the fundus image as input information, and using the area of abnormality in blood circulation specified on the basis of the fluorescein angiography image corresponding to the fundus image as training information, a trained model indicating a relationship between the fundus image and the area of abnormality in blood circulation in the fundus image through learning.

Specifically, in the modified example of the present embodiment, assuming that it is difficult to perform learning and prediction for entire images at once due to memory limitation of a graphics processing unit (GPU), a case where a method for extracting patches from images and causing a neural network to learn the extracted patches is used will be described. Here, as an example, the size of the patch is set to 64 px×64 px, and its stride (interval for moving a frame for patch extraction) is set to 2 px.

The generated patches are divided into two groups of a group containing a positive area and a group containing no positive area. The patches are selected so that the proportions of both groups used for learning become equal.

A phenomenon in which a neural network shows good performance only for learning data itself or an image very similar to the learning data and shows extremely low performance for unknown images is called over-fitting, which may be improved by collecting a larger amount of samples or applying a geometrical operation such as rotation to the learning data.

In the modified example of the present embodiment, after the patches were generated, a rotation angle was determined on the basis of a normal distribution of $\sigma=3$ deg., a horizontal inversion was performed with a probability of 50% and a vertical inversion was performed with a probability of 20%.

Figure 15:
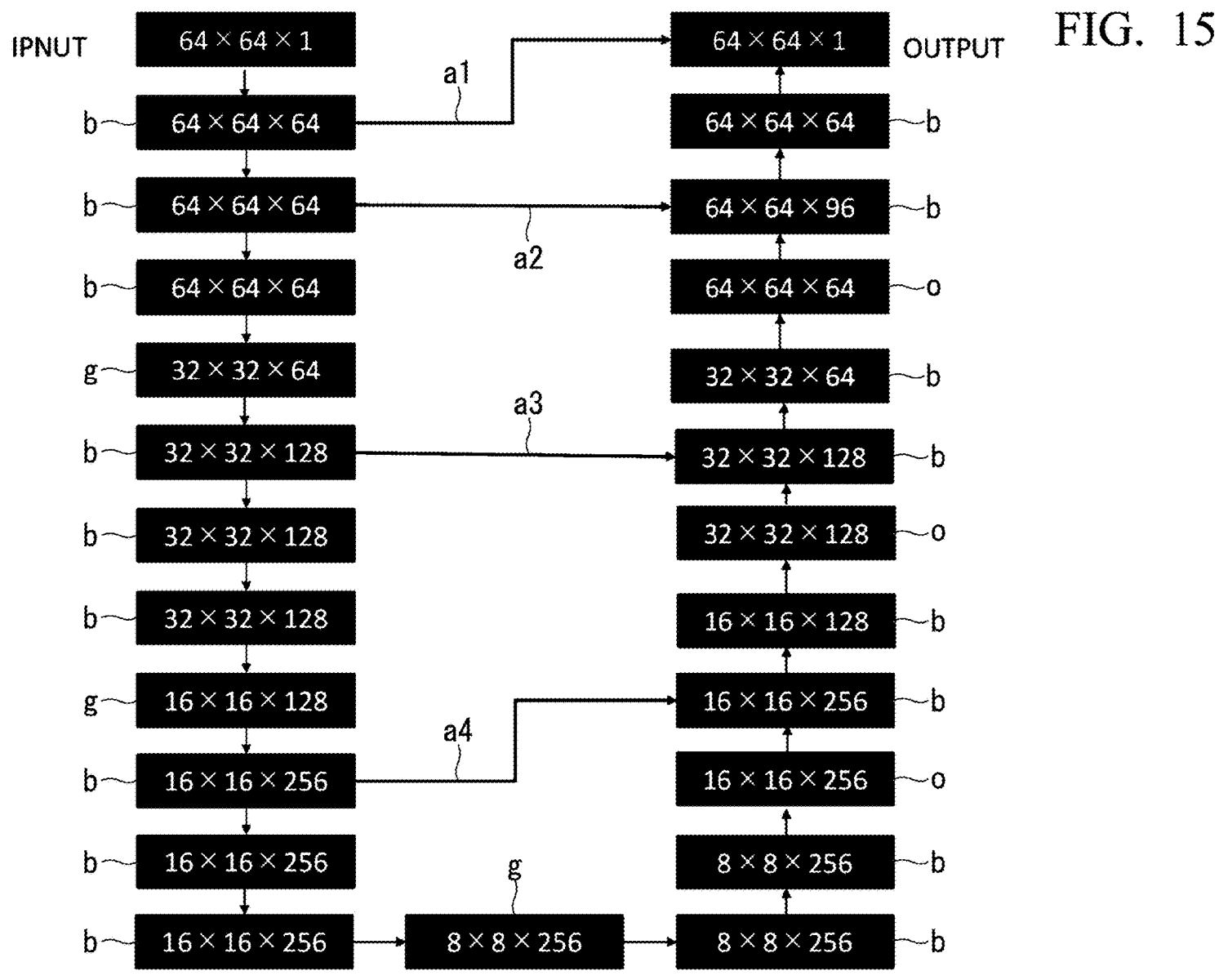

FIG. 15 is a diagram illustrating an example of a structure of a neural network.

One example of the structure of the neural network is based on U-Net. In FIG. 15, b represents convolution (kernel_size=(3,3)), g represents max pooling (pool_size=(2,2)), and o represents up sampling (size=(2,2)). After each convolution layer, a batch normalization was performed using an activation function ReLU. However, in the last convolution layer, the batch normalization was not performed by using sigmoid as an activation function.

Further, arrows indicated by a1, a2, a3, and a4 represent skip connection by concatenation. This is considered to contribute to restoration of image position information.

The learning unit 234 stores the generated trained model in the trained model 216 of the storage unit 210.

The learning unit 234 creates trained model notification information including the created trained model, to be addressed to the diagnosis support device 300, and outputs the created trained model notification information to the communication unit 205.

(Diagnosis Support Device 300)

Figure 16:
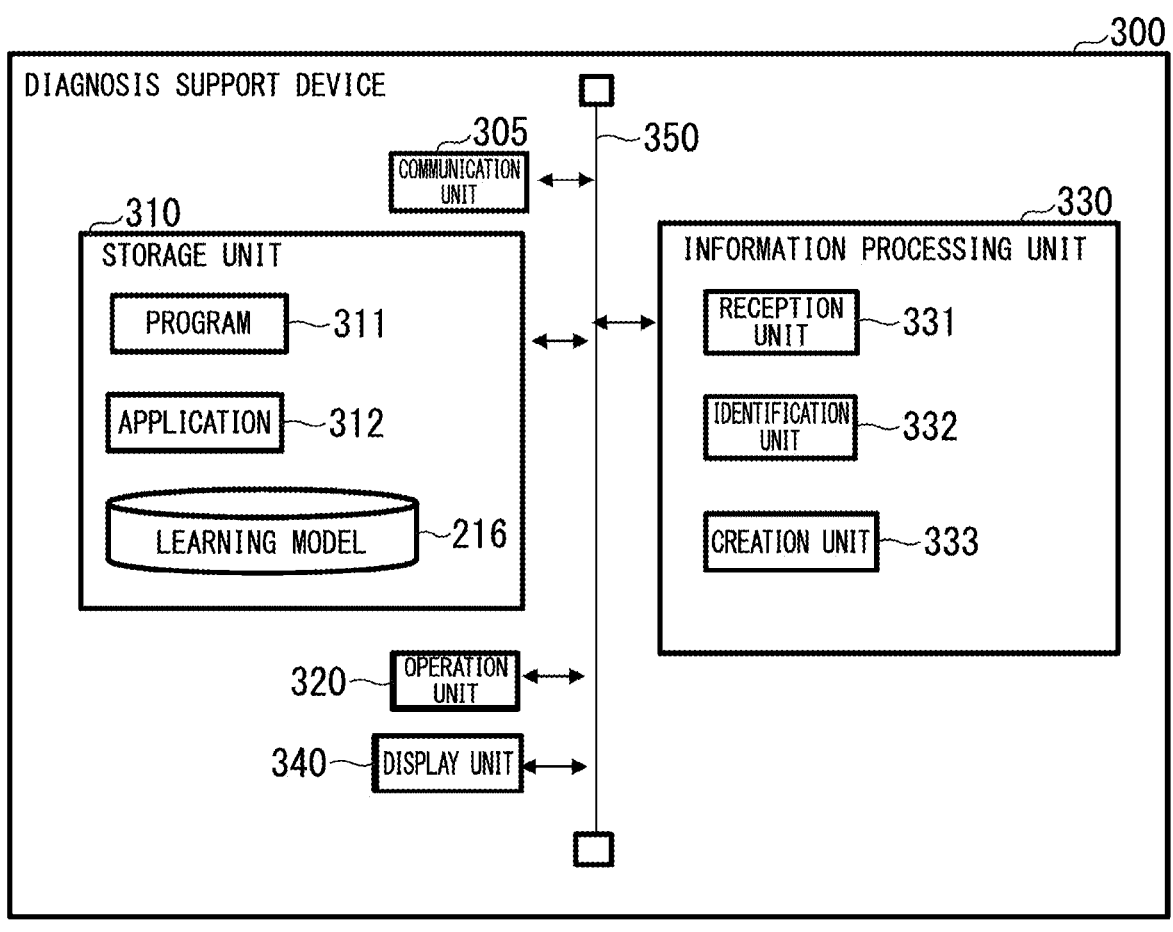
FIG. 16 is a block diagram illustrating an example of a diagnosis support device according to a modified example of the embodiment of the present invention.

FIG. 16 is a block diagram illustrating an example of a diagnosis support device according to a modified example of the embodiment of the present invention.

The diagnosis support device 300 includes a communication unit 305, a storage unit 310, an operation unit 320, an information processing unit 330, a display unit 340, and a bus line 350 such as an address bus or a data bus for electrically connecting the respective components as shown in FIG. 16.

The communication unit 305 is realized by a communication module. The communication unit 305 communicates with external communication devices such as the ophthalmologist terminal 2 or the learning device 200 through the network N. Specifically, the communication unit 305 receives trained model notification information transmitted by the learning device 200, and outputs the received trained model notification information to the information processing unit 330. The communication unit 305 receives patient information transmitted by the ophthalmologist terminal 2, and outputs the received patient information to the information processing unit 330. The communication unit 305 acquires diagnostic information output by the information processing unit 230, and transmits the acquired diagnostic information to the ophthalmologist terminal 2.

The storage unit 310 is realized by, for example, a RAM, a ROM, an HDD, a flash memory, or a hybrid storage device in which a plurality of these memories are combined. The storage unit 310 stores a program 311 executed by the information processing unit 330, an application 312, and a trained model 216.

The program 311 is, for example, an operating system, which is located between a user or an application program and hardware, provides a standard interface for the user or the application program, and performs efficient management for each resource such as hardware.

The application 312 causes the diagnosis support device 300 to receive the trained model notification information transmitted by the learning device 200, and to store the trained model included in the received trained model notification information. The application 312 causes the diagnosis support device 300 to receive the patient information transmitted by the ophthalmologist terminal 2, and to acquire a patient ID and a fundus image included in the received patient information. The application 312 causes the diagnosis support device 300 to recognize an area of abnormality in blood circulation in the acquired fundus image using the stored trained model.

The application 312 causes the diagnosis support device 300 to create diagnostic information including the fundus image of the patient, information indicating the area of abnormality in blood circulation identified using the fundus image of the patient and the trained model, and the patient ID, to be addressed to the ophthalmologist terminal 2, and to transmit the created diagnostic information to the ophthalmologist terminal 2.

The operation unit 320 includes, for example, a touch panel, which detects a touch operation on a screen displayed on the display unit 340 and outputs a detection result of the touch operation to the information processing unit 330.

The display unit 340 includes, for example, a touch panel, which displays a screen that receives information indicating the fundus image included in the patient information received by the diagnosis support device 300. In addition, the display unit 240 displays a result of the diagnosis made by the diagnosis support device 300.

The entirety or a part of the information processing unit 330 is a software function unit realized as a processor such as a CPU executes the program 311 stored in the storage unit 310 and the application 312, for example. The entirety or a part of the information processing unit 330 may be realized by hardware such as LSI, ASIC, or FPGA, or may be realized by a combination of a software function unit and hardware. The information processing unit 330 includes, for example, a reception unit 331, a identification unit 332, and a creation unit 333.

The reception unit 331 acquires the trained model notification information output by the communication unit 305, and acquires the trained model included in the acquired trained model notification information. The reception unit 331 receives the acquired trained model, and stores the received trained model in the trained model 216 of the storage unit 310.

The reception unit 331 acquires the patient information output by the communication unit 305, and acquires the patient ID and the information indicating the fundus image included in the acquired patient information. The reception unit 331 receives the acquired patient ID and the information indicating the fundus image, and outputs the patient ID and the information indicating the fundus image received above to the identification unit 332.

The identification unit 332 acquires the patient ID and the information indicating the fundus image output by the reception unit 331. The identification unit 332 acquires the trained model stored in the trained model 216 of the storage unit 310, and specifies the area of abnormality in blood circulation in the acquired fundus image using the acquired trained model. The identification unit 332 outputs the information indicating the area of abnormality in blood circulation in the identified fundus image and the patient ID to the creation unit 333.

Specifically, in the modified example of the present embodiment, similarly to the learning device 200, a case where a patch is extracted from an image and an area of abnormality in blood circulation in a fundus image is identified using the extracted patch and a trained model will be described. Here, as an example, the size of the patch is set to 64 px×64 px, and its stride (interval for moving a frame for patch extraction) is set to 2 px. All of the generated patches are selected.

The identification unit 332 acquires an image of 64×64×1 on the basis of the trained model. The identification unit 332 votes the acquired pixel values to corresponding pixels of an original image and performs averaging therefor. Here, the identification unit 332 may convert the acquired image into color display.

The creation unit 333 acquires the patient ID and the information indicating the area of abnormality in blood circulation in the fundus image output by the identification unit 332. The creation unit 333 creates the diagnostic information including the acquired patient ID and the information indicating the area of abnormality in blood circulation in the fundus image, to be addressed to the ophthalmologist terminal 2. The creation unit 333 outputs the created diagnostic information to the communication unit 305.

(Operation of Information Processing System)

An example of an operation of the information processing system according to the modified example of this embodiment will be described with reference to FIGS. 17 and 18.

Figure 17:
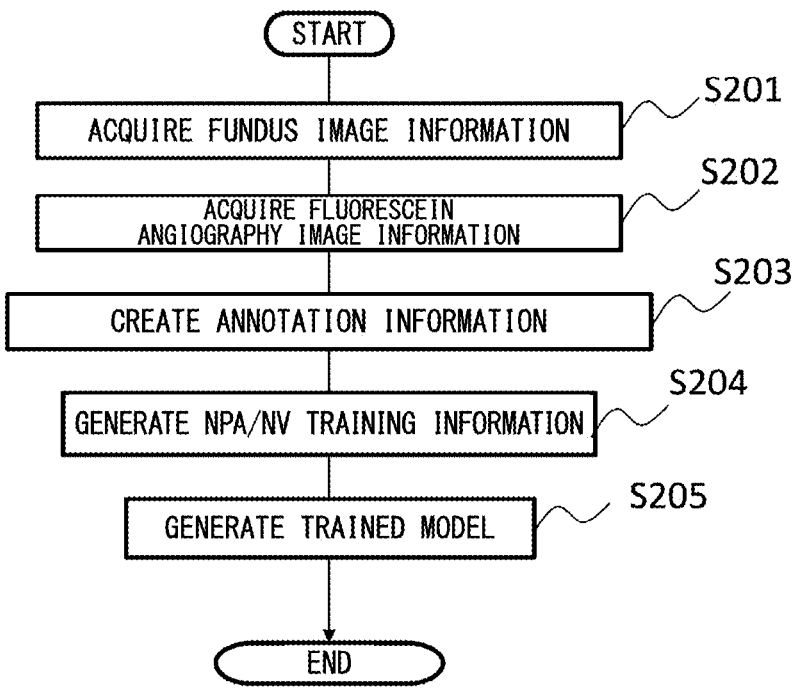
FIG. 17 is a flowchart illustrating an example of an operation of a learning device according to the modified example of the embodiment of the present invention.

FIG. 17 is a flowchart illustrating an example of an operation of a learning device included in the information processing system of the modified example of the present embodiment. FIG. 17 illustrates an operation after the ophthalmologist terminal 2 transmits NPA/NV annotation notification information and accompanying finding annotation notification information to the learning device 200 and the examination device 3 transmits fundus image notification information and fluorescein angiography image notification information to the learning device 200.
(Step S201)

The communication unit 205 of the learning device 200 receives the fundus image notification information transmitted by the examination device 3, and outputs the received fundus image notification information to the information processing unit 230. The image acquisition unit 231 of the information processing unit 230 acquires the fundus image notification information output by the communication unit 205, stores the patient ID and the information indicating the fundus image included in the acquired fundus image notification information in association with each other in the image DB 213 of the storage unit 210.
(Step S202)

The communication unit 205 of the learning device 200 receives the fluorescein angiography image notification information transmitted by the examination device 3, and outputs the received fluorescein angiography image notification information to the information processing unit 230. The image acquisition unit 231 of the information processing unit 230 acquires the fluorescein angiography image notification information output by the communication unit 205, and stores the patient ID and the information indicating the fluorescein angiography image included in the acquired fluorescein angiography image notification information in association with each other in the image DB 213 of the storage unit 210.
(Step S203)

The communication unit 205 of the learning device 200 receives the NPA/NV annotation notification information transmitted by the ophthalmologist terminal 2, and outputs the received NPA/NV annotation notification information to the information processing unit 230. The annotation acquisition unit 232 of the information processing unit 230 acquires the NPA/NV annotation notification information output by the communication unit 205, and stores the patient ID and the NPA/NV annotation information included in the acquired NPA/NV annotation notification information in association with each other in the annotation DB 214 of the storage unit 210.

The communication unit 205 of the learning device 200 receives the accompanying finding annotation notification information transmitted by the ophthalmologist terminal 2, and outputs the received accompanying finding annotation notification information to the information processing unit 230. The annotation acquisition unit 232 of the information processing unit 230 acquires the accompanying finding annotation notification information output by the communication unit 205, stores the patient ID and the accompanying finding annotation information included in the acquired accompanying finding annotation notification information in association with each other in the annotation DB 214 of the storage unit 210.
(Step S204)

The learning information generation unit 233 of the learning device 200 acquires the patient ID, the information indicating the fundus image associated with the patient ID, and the information indicating the fluorescein angiography image stored in the image DB 213 of the storage unit 210. The learning information generation unit 233 acquires the patient ID, the NPA/NV annotation information associated with the patient ID, and the accompanying finding annotation information stored in the annotation DB 214 of the storage unit 210. The learning information generation unit 233 specifies the area of abnormality in blood circulation on the basis of the information indicating the fluorescein angiography image, the NPA/NV annotation information, and the accompanying finding annotation information acquired above. The learning information generation unit 233 generates NPA/NV learning information in which the information indicating the fundus image and the area of abnormality in blood circulation specified on the basis of the fluorescein angiography image corresponding to the fundus image are associated with each other, and stores the generated NPA/NV learning information in the learning information storage 215 of the storage unit 210.
(Step S205)

The learning unit 234 of the learning device 200 acquires the NPA/NV learning information stored in the learning information storage 215 of the storage unit 210. The learning unit 234 acquires information indicating the fundus image and the information indicating the area of abnormality in blood circulation included in the acquired NPA/NV learning information. The learning unit 234 generates, using the acquired information indicating the fundus image as input information, and using the area of abnormality in blood circulation specified on the basis of the fluorescein angiography image corresponding to the fundus image as training information, a trained model indicating a relationship between the fundus image and the area of abnormality in blood circulation in the fundus image through learning. The learning unit 234 stores the generated trained model in the trained model 216 of the storage unit 210.

In the flowchart shown in FIG. 17, the order of steps S201, S202, and S203 may be changed.

According to the flowchart shown in FIG. 17, the learning device 200 may specify the area of abnormality in blood circulation on the basis of the information indicating the fluorescein angiography image, the NPA/NV annotation information, and the accompanying finding annotation information. The learning device 200 may generate, using the information indicating the fundus image as input information, and using the area of abnormality in blood circulation specified on the basis of the fluorescein angiography image corresponding to the fundus image as training information, a trained model indicating a relationship between the fundus image and the area of abnormality in blood circulation in the fundus image through learning.

Figure 18:
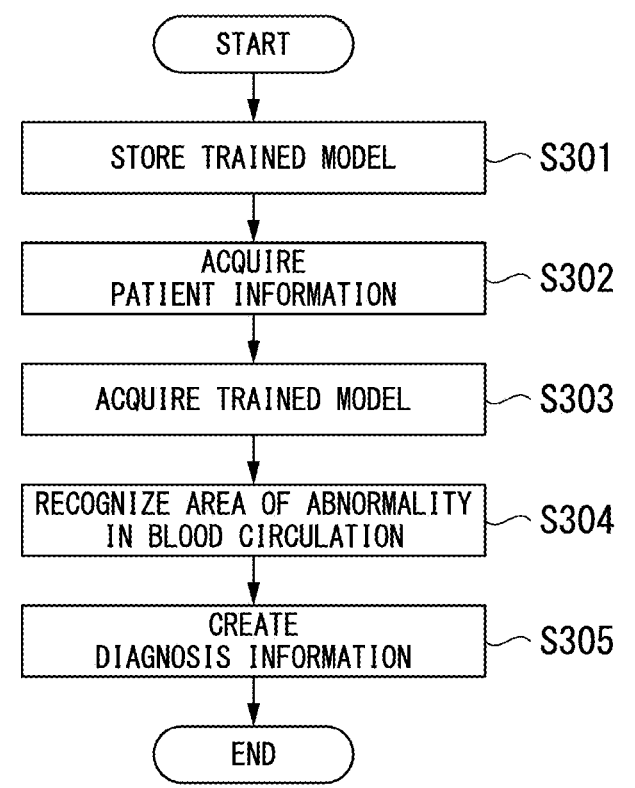
FIG. 18 is a flowchart illustrating an example of an operation of the diagnosis support device according to the modified example of the embodiment of the present invention.

FIG. 18 is a flowchart illustrating an example of an operation of a diagnosis support device included in the information processing system of the modified example of the present embodiment. FIG. 18 shows an operation after the learning device 200 transmits the trained model notification information to the diagnosis support device 300 and the ophthalmologist terminal 2 transmits the patient information to the diagnosis support device 300.
(Step S301)

The communication unit 305 of the diagnosis support device 300 receives the trained model notification information transmitted by the learning device 200, and outputs the received trained model notification information to the information processing unit 330. The reception unit 331 acquires the trained model notification information output by the communication unit 305, and acquires the trained model included in the acquired trained model notification information. The reception unit 331 receives the acquired trained model, and stores the received trained model in the trained model 216 of the storage unit 310.
(Step S302)

The communication unit 305 receives patient information transmitted by the ophthalmologist terminal 2, and outputs the received patient information to the information processing unit 330. The reception unit 331 acquires the patient information output by the communication unit 305, and acquires the patient ID and the information indicating the fundus image included in the acquired patient information. The reception unit 331 receives the acquired patient ID and the information indicating the fundus image, and outputs the patient ID and the information indicating the fundus image received above to the identification unit 332.
(Step S303)

The identification unit 332 acquires the patient ID and the information indicating the fundus image output by the reception unit 331. The identification unit 332 acquires the trained model stored in the trained model 216 of the storage unit 310.
(Step S304)

The identification unit 332 acquires the trained model stored in the trained model 216 of the storage unit 310, and recognizes the area of abnormality in blood circulation in the fundus image that is a identification target using the acquired trained model. The identification unit 332 outputs the information indicating the area of abnormality in blood circulation in the identified fundus image and the patient ID to the creation unit 333.
(Step S305)

The creation unit 333 acquires the patient ID and the information indicating the area of abnormality in blood circulation in the fundus image output by the identification unit 332. The creation unit 333 creates diagnostic information including the patient ID and the information indicating the area of abnormality in blood circulation in the acquired fundus image, to be addressed to the ophthalmologist terminal 2. The creation unit 333 outputs the created diagnostic information to the communication unit 305.

The communication unit 305 acquires the diagnostic information output by the creation unit 333, and transmits the acquired diagnostic information to the ophthalmologist terminal 2.

According to the flowchart shown in FIG. 18, the diagnosis support device 300 may recognize the area of abnormality in blood circulation in the fundus image that is a identification target, using the trained model indicating the relationship between the fundus image generated by using the information indicating the fundus image as input information and using the area of abnormality in blood circulation specified on the basis of the fluorescein angiography image corresponding to the fundus image as training information, and the area of abnormality in blood circulation in the fundus image.

In the above-described modified example, the diagnosis support device 300 receives the trained model notification information transmitted by the learning device 200, and stores the trained model included in the received trained model notification information in the storage unit 310. A case where the diagnosis support device 300 specifies the area of abnormality in blood circulation in the fundus image using the fundus image included in the patient information transmitted by the ophthalmologist terminal 2 and the stored trained model and transmits the diagnostic result including information indicating the identified area of abnormality in blood circulation to the ophthalmologist terminal 2 has been described, but the present invention is not limited to this example. For example, a configuration in which the diagnosis support device 300 transmits the patient information to the learning device 200 may be used. The learning device 200 receives the patient information transmitted by the diagnosis support device 300, and specifies the area of abnormality in blood circulation in the fundus image using the fundus image included in the received patient information and the trained model. The learning device 200 creates a diagnostic result including the information indicating the identified area of abnormality in blood circulation, and transmits the created diagnostic result to the diagnosis support device 300. The diagnosis support device 300 may receive the diagnostic result transmitted by the learning device 200, and may transmit the received diagnostic result to the ophthalmologist terminal 2.

According to the modified example of the present embodiment, the diagnosis support device 300 includes an identification unit that specifies an area of abnormality in blood circulation in a fundus image that is an image of the fundus, using a trained model obtained by learning a relationship between the fundus image and the area of abnormality in blood circulation in the fundus image, on the basis of the fundus image and the area of abnormality in blood circulation specified on the basis of a fluorescein angiography image of the fundus, and an output unit that outputs information indicating the fundus image of a patient and the area of abnormality in blood circulation in the fundus image of the patient identified by the identification unit using the trained model. With this configuration, the diagnosis support device 300 can estimate an abnormal circulation area with high accuracy from a normal fundus image using a trained model in which abnormal circulation area information specified by a doctor from a fluorescein angiography image and a fundus image corresponding thereto are used as training information.

The area of abnormality in blood circulation is generated on the basis of the fluorescein angiography image and an ophthalmologist's diagnostic note regarding one or both of a retinal non-perfusion area and a neovascularization attached to the fluorescein angiography image. With this configuration, it is possible to generate the area of abnormality in blood circulation that serves as the training information on the basis of the fluorescein angiography image and the ophthalmologist's diagnostic note regarding one or both of the retinal non-perfusion area and the neovascularization attached to the fluorescein angiography image.

The identification unit recognizes one or both of the retinal non-perfusion area and an area corresponding to the neovascularization in the fundus image. With this configuration, it is possible to identify one or both of the retinal non-perfusion area and the area corresponding to the neovascularization with high accuracy from the normal fundus image.

The output unit outputs an image in which the area of abnormality in blood circulation identified by the identification unit is overlaid on the fundus image. With this configuration, it is possible to acquire an image in which the abnormal circulation area is superimposed on the normal fundus image from the normal fundus image.

According to the modified example of the present embodiment, the learning device 200 includes a learning unit that generates, on the basis of a fundus image that is an image of the fundus and an area of abnormality in blood circulation specified on the basis of a fluorescein angiography image of the fundus, a trained model indicating a relationship between the fundus image and the area of abnormality in blood circulation in the fundus image, through learning. With this configuration, the learning device 200 can generate the trained model indicating the relationship between the fundus image and the area of abnormality in blood circulation in the fundus image through machine learning.

The area of abnormality in blood circulation is generated on the basis of the fluorescein angiography image and an ophthalmologist's diagnostic note regarding one or both of a retinal non-perfusion area and a neovascularization attached to the fluorescein angiography image. With this configuration, it is possible to generate the area of abnormality in blood circulation that serves as the training information on the basis of the fluorescein angiography image and the ophthalmologist's diagnostic note regarding one or both of the retinal non-perfusion area and the neovascularization attached to the fluorescein angiography image.

The embodiments of the present invention and the modified examples thereof have been described above, but the embodiments and the modified examples thereof are presented as examples, and are not intended to limit the scope of the invention. These embodiments and their modified examples may be implemented in various other forms, and various omissions, replacements, changes, and combinations may be made without departing from the concept of the invention. These embodiments and their modified examples are included in the scope and concept of the invention, and at the same time, are included in the inventions described in claims and their equivalent scopes.

Note that the server 1, the ophthalmologist terminal 2, the examination device 3, the learning device 200, and the diagnosis support device 300 have a computer therein. Further, steps of the respective processes of each device described above are stored in a computer-readable recording medium in the form of a program, and the above processes are performed as the computer reads and executes the program. Here, the computer-readable recording medium includes a magnetic disc, a magneto-optical disc, a CD-ROM, a DVD-ROM, a semiconductor memory, or the like. Further, the computer program may be distributed to the computer through a communication line, and the computer that receives the distribution may execute the program.

In addition, the program may be a program for realizing some of the functions described above.

Further, the program may be a so-called difference file (difference program) capable of realizing the above-mentioned functions in combination with a program already recorded in the computer system.

The following supplementary notes will be disclosed with respect to the above description.

(Supplementary Note 1)

A program that causes a computer that controls an information processing device to execute a control process including: a fluorescein angiography image acquisition step of acquiring fluorescein angiography image information; an NPA/NV annotation acquisition step of acquiring a diagnostic note of an ophthalmologist regarding at least one of a retinal non-perfusion area or a neovascularization, attached to the fluorescein angiography image information, as NPA/NV annotation information; an NPA/NV training information generation step of generating NPA/NV training information that is training information for calculating an existence probability of the retinal non-perfusion area and an existence probability of the neovascularization, on the basis of the fluorescein angiography image information and the NPA/NV annotation information corresponding to the fluorescein angiography image information; a fundus image acquisition step of acquiring fundus image information; an NPA/NV existence probability calculation step of calculating the existence probability of the retinal non-perfusion area and the existence probability of the neovascularization in the fundus image information on the basis of the NPA/NV training information; and an estimated NPA/NV identification step of recognizing an area of the fundus image information that is estimated to correspond to the retinal non-perfusion area, as an estimated NPA, and recognizing an area that is estimated to correspond to the neovascularization, as an estimated NV, on the basis of the existence probability of the retinal non-perfusion area and the existence probability of the neovascularization.

(Supplementary Note 2)

The program according to supplementary note 1 that causes the computer to execute the control process further including: an NPA/NV existence probability map generation step of generating an NPA/NV existence probability map in which the NPA existence probability and the NV existence probability are identifiably displayed in the fundus image information.

(Supplementary Note 3)

The program according to supplementary note 1 or 2 that causes the computer to execute the control process further including: an accompanying annotation acquisition step of acquiring, as accompanying finding annotation information, a diagnostic note of the ophthalmologist regarding an accompanying finding, attached to the fluorescein angiography image information and the fundus image information; an accompanying finding training information generation step of generating accompanying finding training information that serves as training information for calculating an existence probability of the accompanying finding in the fundus image information, on the basis of the fluorescein angiography image information and the fundus image information, and the accompanying finding annotation information corresponding to the fluorescein angiography image information and the fundus image information; and an accompanying finding existence probability calculation step of calculating the existence probability of the accompanying finding in the fundus image information on the basis of the accompanying finding training information, and in which in the NPA/NV existence probability calculation step, a control process of calculating the existence probability of the retinal non-perfusion area and the existence probability of the neovascularization in the fundus image information, on the basis of the accompanying finding existence probability and the NPA training information is executed.

(Supplementary Note 4)

The program according to supplementary note 3 that causes the computer to execute the control process further including: an accompanying finding existence probability map generation step of generating an accompanying finding existence probability map in which the existence probability of the accompanying finding is identifiably displayed in the fundus image information.

(Supplementary Note 5)

An information processing method executed by an information processing device, the method including: a fluorescein angiography image acquisition step of acquiring fluorescein angiography image information; an NPA/NV annotation acquisition step of acquiring a diagnostic note of an ophthalmologist regarding at least one of a retinal non-perfusion area or a neovascularization, attached to the fluorescein angiography image information, as NPA/NV annotation information; an NPA/NV training information generation step of generating NPA/NV training information that is training information for calculating an existence probability of the retinal non-perfusion area and an existence probability of the neovascularization, on the basis of the fluorescein angiography image information and the NPA/NV annotation information corresponding to the fluorescein angiography image information; a fundus image acquisition step of acquiring fundus image information; an NPA/NV existence probability calculation step of calculating the existence probability of the retinal non-perfusion area and the existence probability of the neovascularization in the fundus image information, on the basis of the NPA/NV training information; and an estimated NPA/NV identification step of recognizing an area of the fundus image information that is estimated to correspond to the retinal non-perfusion area, as an estimated NPA, and recognizing an area that is estimated to correspond to the neovascularization, as an estimated NV, on the basis of the existence probability of the retinal non-perfusion area and the existence probability of the neovascularization.

(Supplementary Note 6)

An information processing device including: fluorescein angiography image acquisition means for acquiring fluorescein angiography image information; NPA/NV annotation acquisition means for acquiring a diagnostic note of an ophthalmologist regarding at least one of a retinal non-perfusion area or a neovascularization, attached to the fluorescein angiography image information, as NPA/NV annotation information; NPA/NV training information generation means for generating NPA/NV training information that is training information for calculating an existence probability of the retinal non-perfusion area and an existence probability of the neovascularization, on the basis of the fluorescein angiography image information and the NPA/NV annotation information corresponding to the fluorescein angiography image information; fundus image acquisition means for acquiring fundus image information; NPA/NV existence probability calculation means for calculating the existence probability of the retinal non-perfusion area and the existence probability of the neovascularization in the fundus image information, on the basis of the NPA/NV training information; and estimated NPA/NV identification means for recognizing an area of the fundus image information that is estimated to correspond to the retinal non-perfusion area, as an estimated NPA, and recognizing an area that is estimated to correspond to the neovascularization, as an estimated NV, on the basis of the existence probability of the retinal non-perfusion area and the existence probability of the neovascularization.

REFERENCE SIGNS LIST

1: Server
2: Ophthalmologist terminal
3: Examination device
11: CPU
12: ROM
13: RAM
14: Bus
15: Input/output interface
16: Display unit
17: Input unit
18: Storage unit
19: Communication unit
20: Drive
30: Removable medium
101: Image acquisition unit
102: Annotation acquisition unit 103: Training information generation unit
104: Arithmetic unit
105: Map generation unit
106: Estimated NPA/NV identification unit
107: Estimated NPA/NV display control unit
200: Learning device
205: Communication unit
210: Storage unit
211: Program
212: Application
213: Image DB
214: Annotation DB
215: Learning information
216: Trained model
220: Operation unit
230: Information processing unit
231: Image acquisition unit
232: Annotation acquisition unit
233: Learning information generation unit
234: Learning unit
240: Display unit
250: Bus line
300: Diagnosis support device
305: Communication unit
310: Storage unit
311: Program
312: Application
320: Operation unit
330: Information processing unit
331: Reception unit
332: Identification unit
333: Creation unit
240: Display unit
350: Bus line
401: Image DB
402: Annotation DB
403: Training DB
A: Estimated NPA
B: Estimated NV
C: Fluorescein angiography image information
D: Ophthalmologist
E: NPA/NV existence probability map
F: Fundus image information

What is claimed is:

1. A method for supporting diagnosis comprising:
receiving a fundus image,
processing the fundus image using a trained model configured to recognize an area of abnormality in blood circulation in the fundus image, wherein the trained model has been trained based upon a training data set comprising plurality sets of a training fundus image, a fluorescent angiography image, and information of blood circulation abnormality associated with the fluorescent angiography image, the information of blood circulation abnormality associated with the fluorescent angiography image comprising an annotation regarding a retinal non-perfusion area and/or an area corresponding to a neovascularization, and
outputting information relating to the area of abnormality in blood circulation in the fundus image,
wherein the fluorescent angiography image and the training fundus image are acquired from a same patient.

2. The method for supporting diagnosis according to claim 1,
wherein the fluorescent angiography image corresponds to the training fundus image.

3. The method for supporting diagnosis according to claim 1, wherein the fundus image is the image obtained without performing fundus fluorescein angiography.

4. The method for supporting diagnosis according to claim 1, wherein the area of abnormality in blood circulation in the fundus image is recognized by specifying a feature common in the training fundus image associated with information of blood circulation abnormality.

5. The method for supporting diagnosis according to claim 1, wherein information relating to the area of abnormality in blood circulation in the fundus image comprise of an image in which the area of abnormality in blood circulation is overlaid on the fundus image.

6. The method for supporting diagnosis according to claim 1, wherein positions of eyeballs of the training fundus image and the fluorescein angiography image coincide with each other.

7. The method for supporting diagnosis according to claim 1, wherein the training data set comprise of a green component of the training fundus image and the fluorescein angiography image.

8. The method for supporting diagnosis according to claim 1 further comprising, calculating an existing probability of a retinal non-perfusion area and/or an area corresponding to a neovascularization in the fundus image.

9. The method for supporting diagnosis according to claim 8, wherein the non-perfusion area existence probability and/or a neovascularization existence probability is calculated by, extracting a feature common in the training fundus image having the non-perfusion and/or neovascularization area; and normalizing a matching degree with the feature with respect to the fundus image.

10. The method for supporting diagnosis according to claim 1 further comprising, generating an existence probability map in which the non-perfusion area existence probability and/or a neovascularization existence probability are identifiably displayed in the fundus image.

11. A device for supporting diagnosis, comprising:

a memory;

a processor connected to the memory and that:

receive a fundus image, process the fundus image using a trained model configured to recognize an area of abnormality in blood circulation in the fundus image, wherein the trained model has been trained based upon a training data set comprising plurality sets of a training fundus image, a fluorescent angiography image, and information of blood circulation abnormality associated with the fluorescent angiography image, the information of blood circulation abnormality associated with the fluorescent angiography image comprising an annotation regarding a retinal non-perfusion area and/or an area corresponding to a neovascularization, and output information relating to the area of abnormality in blood circulation in the fundus image, wherein the fluorescent angiography image and the training fundus image are acquired from a same patient.

12. The device for supporting diagnosis according to claim 11, wherein the fluorescent angiography image and the fluorescent angiography image are in association with each other.

13. A non-transitory computer readable medium, storing a program causing a computer to execute:

receiving a fundus image, processing the fundus image using a trained model configured to recognize an area of abnormality in blood circulation in the fundus image of the subject eye, wherein the trained model has been trained based upon a training data set comprising plurality sets of a training fundus image, a fluorescent angiography image and an information of blood circulation abnormality associated with the fluorescent angiography image, the information of blood circulation abnormality associated with the fluorescent angiography image comprising an annotation regarding a retinal non-perfusion area and/or an area corresponding to a neovascularization, and outputting information relating to the area of abnormality in blood circulation in the fundus image, wherein the fluorescent angiography image and the training fundus image are acquired from a same patient.

* * * * *